United States Patent [19]
Mann et al.

[11] Patent Number: 4,940,052
[45] Date of Patent: Jul. 10, 1990

[54] MICROPROCESSOR CONTROLLED RATE-RESPONSIVE PACEMAKER HAVING AUTOMATIC RATE RESPONSE THRESHOLD ADJUSTMENT

[75] Inventors: Brian M. Mann, Los Angeles; John W. Poore, South Pasadena, both of Calif.

[73] Assignee: Siemens-Pacesetter, Inc., Sylmar, Calif.

[21] Appl. No.: 301,934

[22] Filed: Jan. 25, 1989

[51] Int. Cl.$^5$ .............................................. A61N 1/00
[52] U.S. Cl. ........................ 128/419 PG; 128/419 PS
[58] Field of Search ........ 128/419 P, 419 PG, 419 PS

[56] References Cited

U.S. PATENT DOCUMENTS

| | | | |
|---|---|---|---|
| Re. 30,366 | 8/1980 | Rasor et al. ...................... | 128/419 P |
| 3,659,615 | 5/1972 | Enger .............................. | 128/419 B |
| 3,777,762 | 12/1973 | Nielsen ............................ | 128/419 P |
| 4,164,944 | 8/1979 | Alley, III et al. ............. | 128/419 PG |
| 4,201,219 | 5/1980 | Bonzal Gonzalez ......... | 128/419 PG |
| 4,481,950 | 11/1984 | Duggan ........................ | 128/419 PT |
| 4,485,813 | 12/1984 | Anderson et al. .................. | 128/675 |
| 4,545,380 | 10/1985 | Schroeppel ...................... | 128/419 P |
| 4,554,920 | 11/1985 | Baker, Jr. et al. ........... | 128/419 PG |
| 4,554,921 | 11/1985 | Boute et al. .................. | 128/419 PG |
| 4,554,922 | 11/1985 | Prystowsky et al. ........ | 128/419 PG |
| 4,566,456 | 1/1986 | Koning et al. ............... | 128/419 PG |
| 4,712,555 | 12/1987 | Thornander et al. ........ | 128/419 PG |
| 4,773,401 | 9/1988 | Citak et al. .................. | 128/419 PG |
| 4,790,318 | 12/1988 | Elimqvist et al. ........... | 128/419 PG |
| 4,803,987 | 2/1989 | Calfee et al. ................. | 128/419 PG |

OTHER PUBLICATIONS

Broch, "Effects of Vibrations and Shock on Man", Mechanical Vibration and Shock Movements, (Brouel & Kjaer, Oct. 1980), pp. 85–96.
Servais et al., "Estimating Human Energy Expenditure Using an Accelerometer Device", (IEEE, 1982), pp. 371–374.
Wong et at., "Portable Accelerometer Device for Measuring Human Energy Expenditure", (IEEE Transactions on Biomedical Engineering, 1981), pp. 467–471.
PCT International Appl. No. PCT/DE85/00173, Load–Related Variable Frequency Pacemaker, by Eckhard Alt.
Ionèscu, "First Asian–Pacific Symposium on Cardiac Pacing", (PACE, May–Jun. 1980), pp. 357; 375.

*Primary Examiner*—Francis Jaworski
*Assistant Examiner*—George Manuel
*Attorney, Agent, or Firm*—Leslie S. Miller; Bryant R. Gold; Lisa P. Weinberg

[57] ABSTRACT

A rate-responsive pacemaker which includes a conventional programmable pulse generator, a physiological sensor, and a processor is disclosed which generates heart stimulation pulses on demand, or as otherwise programmed, as controlled by a rate control signal which is derived from the physiological sensor. The physiological sensor generates a raw signal which varies as a function of some physiological parameter, such as activity level to provide some indication of whether the heart rate should increase or decrease, and hence whether the pacemaker should change the rate at which pacing pulses are provided. The processor converts the raw signal to the sensor-indicated rate signal in accordance with a selectable transfer relationship which defines the sensor-indicated rate signal as a function of a set of discrete sensor level index signals. The sensor-indicated rate signal remains at a minimum value or base rate for all sensor level index signals below a prescribed rate response threshold, with this rate response threshold being set automatically by the processor as a function of a running average of the sensor level index signals monitored over a prescribed time period.

47 Claims, 11 Drawing Sheets

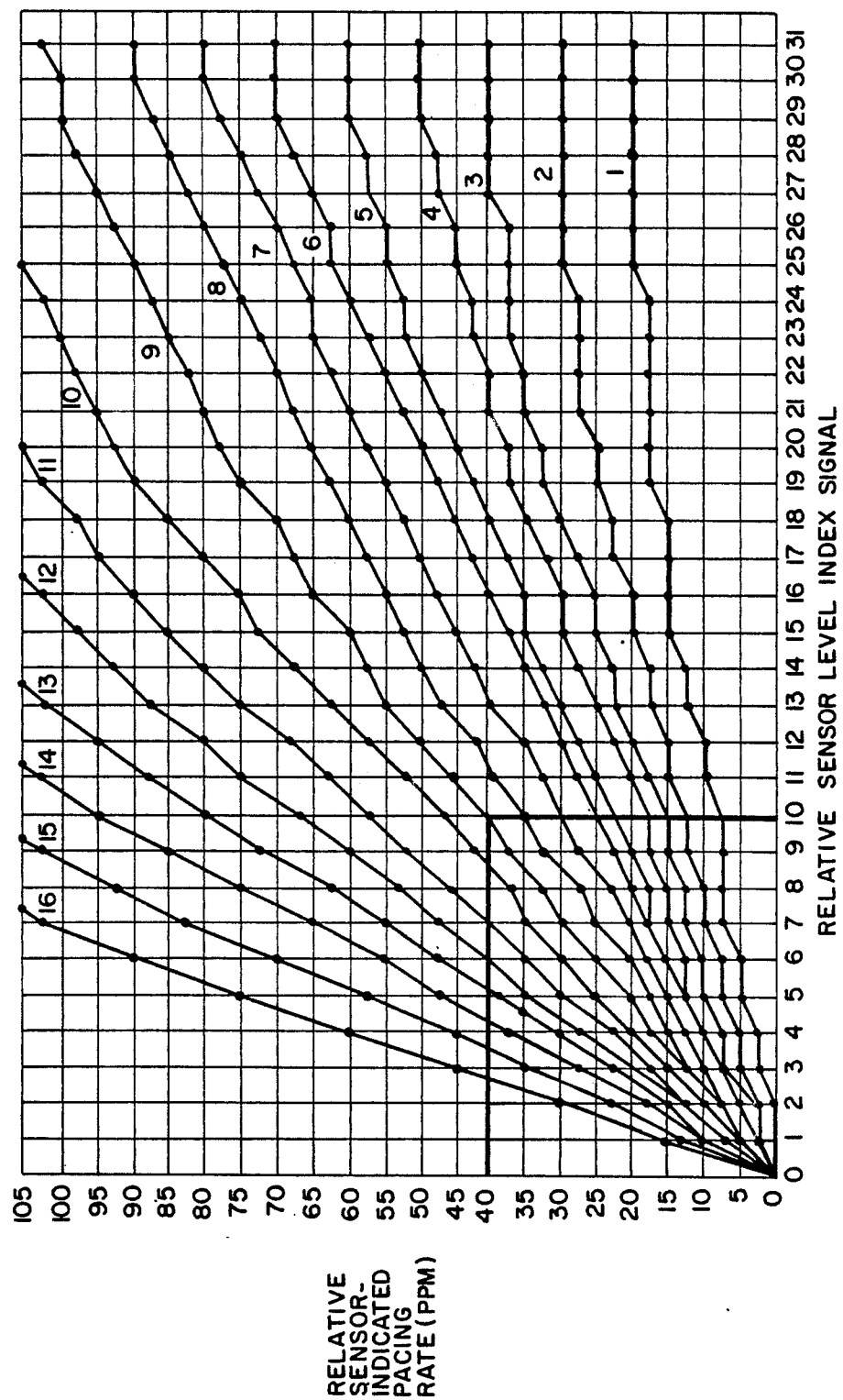

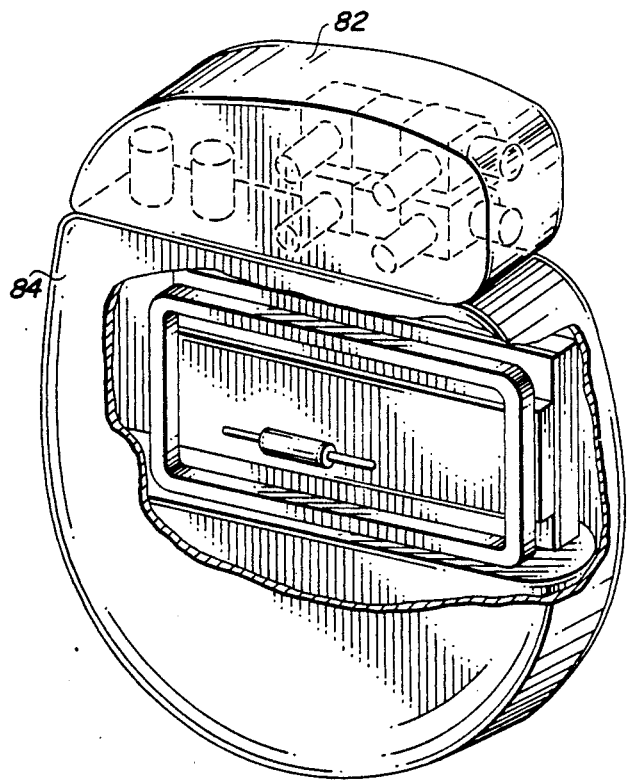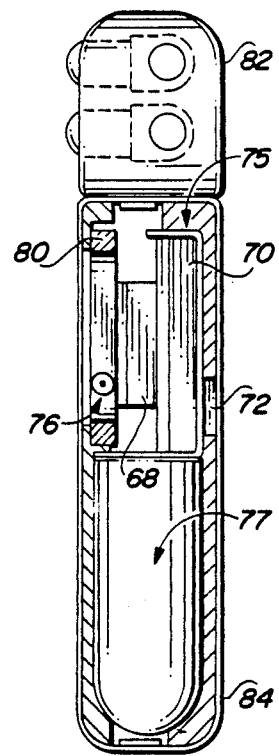
*FIG.7*   *FIG.8*
| SENSOR-INDICATED RATE HISTOGRAM | | |
|---|---|---|
| TOTAL TIME SAMPLED: 0d 0h 0m 30s — SAMPLING RATE: 1.6 SECONDS | | |
| BIN NUMBER | RANGE (PPM) | SAMPLE COUNTS |
| 1 | 70 - 79 | 7 |
| 2 | 79 - 88 | 4 |
| 3 | 88 - 96 | 2 |
| 4 | 96 - 105 | 2 |
| 5 | 105 - 114 | 1 |
| 6 | 114 - 123 | 1 |
| 7 | 123 - 131 | 2 |
| 8 | 131 - 148 | 0 |
|  | TOTAL | 19 |
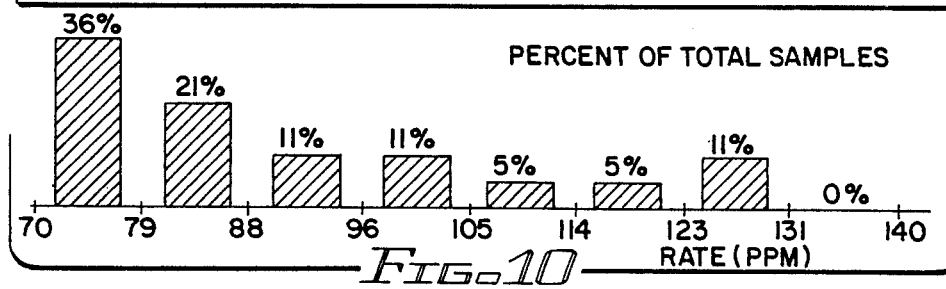
*FIG.10*

MICROPROCESSOR CONTROLLED RATE-RESPONSIVE PACEMAKER HAVING AUTOMATIC RATE RESPONSE THRESHOLD ADJUSTMENT

BACKGROUND OF THE INVENTION

1. Field of the Invention

The present invention relates generally to rate responsive cardiac pacemakers, and more particularly to an implantable microprocessor-controlled rate-responsive pacemaker wherein a programmed rate or a sensor-indicated rate may be selectively used to determine the rate at which pulses are generated on demand, or as otherwise programmed, by the pacemaker; one feature of the invention is an automatically adjustable rate response threshold which a sensed physiological parameter must exceed before a rate-responsive function is provided.

A pacemaker is an implantable medical device which delivers electrical stimulation pulses to a patient's heart in order to keep the heart beating at a desired rate. Early pacemakers provided stimulation pulses at a fixed rate or frequency, such as 70 pulses per minute (ppm), thereby maintaining the heart beat at that fixed rate. Subsequently, pacemakers were designed to not only stimulate the heart, but also to monitor the heart. If a natural heart beat was detected within a prescribed time period (usually referred to as the "escape interval"), no stimulation pulse was delivered, thereby allowing the heart to beat on its own without consuming the limited power of the pacemaker. Such pacemakers are referred to as "demand pacemakers" because stimulation pulses are provided only as demanded by the heart.

Early demand pacemakers had a fixed base rate associated with them. In later versions, the base rate was programmably selectable, and thereafter became commonly known as the "programmed rate." If the heart was able to beat on its own at a rate exceeding the base (or programmed) rate, then no stimulation pulses were provided. However, if the heart was not able to beat on its own at a rate exceeding the base rate, then stimulation pulses were provided to ensure that the heart would always beat at least at the base (or programmed) rate. Such operation was achieved by simply monitoring the heart for a natural beat during the escape interval. If natural activity was sensed, the timer which defined the escape interval was reset. If no natural activity was sensed, a stimulation pulse was provided as soon as the escape interval had timed out. Changing the base (or programmed) rate was accomplished by simply changing the duration of the escape interval.

In recent years, rate-responsive pacemakers have been developed which automatically change the rate at which the pacemaker provides stimulation pulses as a function of a sensed physiological parameter. The physiological parameter provides some indication of whether the heart should beat faster or slower, depending upon the physiological needs of the pacemaker user. Thus, for example, if a patient is at rest, there is generally no need for a faster-than-normal heart rate, so the rate-responsive pacemaker maintains the "base rate" at a normal value, such as 60 pulses per minute (ppm).

However, if the patient is exercising, or otherwise physiologically active, there is a need for the heart to beat much faster, such as, for example, 100 beats per minute. For some patients, the heart is not able to beat faster on its own, so the pacemaker must assist. In order to do this effectively, the physiological need for the heart to beat faster must first be sensed, and the "base rate" of the rate-responsive pacer must be adjusted accordingly. Hence, rate-responsive pacemakers are known in the art which increase and decrease the "base rate" as a function of sensed physiological need.

Numerous types of sensors are taught in the art for use with a rate-responsive pacer. One common type of sensor is an activity sensor which senses the physical activity level of the patient. See, for example, U.S. Pat. Nos. 4,140,132, to Dahl, and 4,485,813, to Anderson et al. In accordance with the teachings of Dahl or Anderson et al., a piezo-electric crystal is used as an activity sensor. Such a crystal generates an electrical signal when subjected to physical movement and stress according to well known principles.

The electrical signal generated by the crystal may be processed by rectifying and filtering it as taught by Dahl, or by monitoring the frequency of the highest amplitude peaks as taught by Anderson et al. An increase or decrease in the parameter being monitored signals a need to increase or decrease the rate at which pacing pulses are provided. Note, as used herein, the term "pacing rate" refers to the rate at which the pacer provides stimulation pulses, or in the case of demand pacers, the rate at which the pacer would provide stimulation pulses in the absence of naturally occurring heart beats. Also, for purposes of this application, the terms "pacer" and "pacemaker" are used interchangeably.

Other types of sensors used in prior art rate-responsive pacers include sensors that sense respiration rate, blood oxygen level, blood and/or body temperature, blood pressure, the length of the Q-T interval, the length of the P-R interval, etc. Rate-responsive pacers using these other types of sensors have yet to demonstrate their commercial viability. To applicants' knowledge, only the piezoelectric sensor has been marketed successfully in significant numbers to date. However, any or all of these other types of sensors may prove efficacious in the future. Advantageously, the invention presented herein may be used with any of these prior art sensors, or with any other physiological sensors yet to be developed.

Even when a reliable or quasi-reliable indicator of physiological need is used in a rate-responsive pacer, however, there is still a need to customize the manner in which a particular patient reacts to the output signals from the chosen sensor. While some flexibility exists in this regard in the manner in which a pacemaker is programmed, the available programming options relative to the rate-responsive features have heretofore been severely limited. Further, even when a pacemaker is initially programmed in a suitable manner, there is no guarantee that this manner of programming will remain suitable over a long period of time.

In addition, while reprogramming may typically be performed, such reprogramming requires additional visits to the doctor, which visits can become quite burdensome for the patient. Hence, there is a need in the art for a rate-responsive pacer that provides greater flexibility in the manner in which the pacer is initially programmed, and which thereafter provides automatic adjustment of some of the key parameters which influence the effectiveness of the pacer.

Moreover, because all rate-responsive pacers include some type of sensor or sensing mechanism to sense at what rate the heart should be paced, there is a critical need to ensure that the sensor, and its related circuitry, function properly. Should the sensor fail, or should any of the circuits associated with the sensor fail, the pacer must still continue to provide stimulation pulses, if required, at a safe rate. In this regard, it is noted that normally, because of the stringent design and manufacturing requirements imposed on an implantable medical product, failure of the pacemaker or the pacemaker circuits and elements is an extremely unlikely event. However, because the sensors used with a rate-responsive pacer involve additional parts, and because the operation of such sensors typically involves measuring or sensing very ill-defined and/or low level signals, and further because the processing circuitry used with such sensors is by necessity quite sophisticated and complex in order to extract the relevant information from the low level signals, the possibility of a circuit failure in a rate-responsive pacer is increased. Hence, what is needed in the art is a fail-safe mechanism within the rate-responsive pacer which may be used to provide stimulation pulses at a safe rate in the event of failure of the sensor and/or rate-responsive portions of the pacemaker circuits.

Similarly, because of the above-mentioned complexity and sophistication of most rate-responsive pacers, such pacers are typically expensive to design, manufacture, test, and maintain. It is not uncommon, for example, for a particular design approach to be taken relative to a proposed rate-responsive pacer design, only to discover several months or years later that the approach is not the best approach that should or could be taken. Further, because of the miniaturization of the circuits used in modern implantable pacers, any significant design change usually requires starting over with the design of a new custom integrated circuit chip. Such a process of starting over once a new approach is taken is not only time consuming, but is also extremely expensive.

What is needed, therefore, is a rate-responsive pacer configuration which allows the use of a tried and proven pacemaker chip (pulse generator and related controls) for the basic pacemaker functions, yet allows a versatile, easy-to-change processing circuit chip, used with a selected sensor, for the rate-responsive functions. This is a primary objective of the present invention. Finally, the present invention must attain all of the aforesaid advantages and objectives without incurring any substantial relative disadvantage.

SUMMARY OF THE INVENTION

The disadvantages and limitations of the background art discussed above are overcome by the present invention. With this invention, a versatile rate-responsive pacemaker which addresses the needs identified above as well as other needs is provided. In particular, the present invention provides a dual chamber, activity-responsive, multimode, multiprogrammable implantable cardiac pacemaker. The pacemaker includes an otherwise conventional programmable pacemaker chip, a microprocessor chip, a physiological sensor, and a battery, all housed within the same implantable enclosure.

The programmable pacemaker chip provides all of the conventional programmable pacemaker functions, including generating pacing pulses in one of many possible modes of operation, sensing cardiac activity from one or both chambers of the heart, and providing a selected programmed response. The microprocessor chip includes a powerful processing means for interfacing between the physiological sensor and the control circuits of the pacemaker chip. Such a processor generates a sensor-indicated rate signal which varies as a function of the raw signal obtained from the sensor. Such a sensor-indicated rate signal, if programmably selected to be used by the pacemaker circuits (SENSOR ON), provides a basis for automatically adjusting the pacing rate of the pacemaker as a function of the physiological needs sensed by the sensor. If the sensor-indicated rate signal is not selected (SENSOR OFF), the pacemaker provides a pacing rate as programmed in conventional manner.

In the preferred embodiment, the sensor is a piezoelectric sensor which is bonded to the inside of the pacemaker enclosure. This sensor generates a raw signal which results from deflections of the enclosure occurring with patient activity. This raw signal is processed by the microprocessor chip and converted to the sensor-indicated rate signal, which sensor-indicated rate signal is used to selectively control the pacemaker circuits.

Further, memory circuits included within or connected to the microprocessor chip allow data to be stored relative to the past performance of the rate-responsive pacer. These memory circuits may be noninvasively interrogated and the data displayed as a histogram which shows the distribution of the sensor-indicated rate data over the recording period. Advantageously, this data may be subsequently studied by appropriate medical personnel, at a time convenient to all concerned, to verify that the pacer is optimally programmed and/or functioning within expectations. Additionally and alternatively, in one embodiment, such data is used by the on-board microprocessor chip to automatically adjust the rate response threshold operation of the rate-responsive portions of the pacemaker circuits.

In the event the sensor or the microprocessor chip should fail, the pacemaker chip can function independently from the microprocessor and sensor, thereby providing conventional or life-sustaining pacemaker operation. Thus, the system provides a fail-safe mechanism wherein all conventional pacing functions are still provided even in the event of a complete failure of the microprocessor and/or sensor.

It is thus a feature of the present invention to provide, in a single implantable case or enclosure, the combination of a standard programmable pacemaker chip, a microprocessor chip, and a physiological sensor. Such a combination advantageously allows many different and varied configurations and approaches to be taken relative to how the sensor signal is processed and used; and allows, if desired, the sensor circuits to be selectively disabled (SENSOR OFF), thereby resulting in a conventional programmable pacemaker.

It is a further feature of the present invention to provide a rate-responsive pacer that provides a desired pacemaker response to the signals generated by a physiological sensor, yet a response which may be easily altered during design, manufacturing, testing or patient-use phases. Further, because of the versatile programming features included within both the conventional and rate-responsive portions of the pacer, the pacemaker may be readily configured to suit the unique needs of any given patient at any given time.

One feature of the rate-responsive pacer herein described allows the rate response threshold at which the rate-responsive functions of the pacer take effect to be selectively adjusted to suit the needs of a particular patient. Coupled with this rate response threshold-setting ability is the capability of programmably selecting a particular response characteristic, such as the rate at which the sensor-indicated rate changes as a function of sensed changes in the signal from the sensor (slope), how quickly the sensor-indicated rate increases as a function of time (reaction time), and how rapidly the sensor-indicated rate decreases as a function of time (recovery time).

Another feature of one embodiment of the present invention allows the rate increase from the baseline rate response threshold of the rate-responsive pacer to be automatically set based upon the sensed physiological activity level of the patient over a prior period of time, such as, for example, the previous 18 hours.

Yet another feature of the rate-responsive pacer of the present invention monitors and records the performance of the sensor over a predetermined fixed, sliding window of time preceding the present time, regardless of whether or not the sensor mode of operation is selected.

In summary, the present invention includes a pulse generator means for generating a pacing pulse at a rate set by a rate control signal, means for generating a base rate signal, sensor means for generating a raw sensor signal, processor means for generating a pacing rate signal as a function of the raw sensor signal, and selection means for selecting one of the base rate signal or the pacing rate signal as the rate control signal for the pulse generator means. This configuration allows the pulse generator means to generate the pacing pulses at a rate determined by the selected one of the base rate signal or the pacing rate signal.

The processor means includes a preprocessing means for converting the raw sensor signal to one of a plurality of sensor level index signals, and conversion means for converting the sensor level index signal into the sensor-indicated rate signal. In one embodiment, the sensor level index signal is digitized and assumes a value of from zero to thirty-one (thirty-two possible values).

The sensor-indicated rate signal assumes a value as a function of a selected one of a family of transfer characteristic curves, or tables, each curve or table relating the sensor level index signal on one axis or column to the sensor-indicated rate signal on the other axis or row. For sensor level index signals below a prescribed minimum rate response threshold, the sensor-indicated rate signal is a fixed minimum value. Similarly, for most transfer curves within the family of transfer curves, the sensor-indicated rate signal for sensor level index signals above a prescribed maximum rate response level is a fixed maximum value.

The minimum rate response threshold of the sensor signal at which the rate-responsive functions become effective may be programmably set to any desired value. In one embodiment, this minimum rate response threshold is set automatically based upon an average, or other processed value, of the activity level of the patient over a prescribed period of time.

The invention described herein further contemplates a method of setting the rate response threshold at which the rate-responsive functions of a pacer as above described are effective, i.e., the minimum rate response threshold of the sensor level index signal below which the sensor-indicated rate signal remains constant. This method includes the steps of subjecting the pacemaker and its sensor to a low level of activity, sampling the sensor indicated rate signal derived from the sensor at a first prescribed sampling rate during the low level activity period, sorting and storing each sampled sensor indicated rate signal in a memory device as a function of its value, retrieving and displaying the stored values of the sampled sensor indicated rate signals, selecting a sensor index level rate response threshold to be at least a value that corresponds to the highest sensor indicated rate signal displayed during the low activity period.

Other variations of the method include adding an offset value to the sensor level index signal derived as described above in order to arrive at the rate response threshold. Thus, for example, if the maximum sensor level index signal during a period of low activity is determined to have a value of four, and if the offset value is selected to have a value of two, then the rate response threshold of the sensor level index signal would be set at a value of six. In such an example, the sensor-indicated rate signal remains at a minimum value, such as 60 ppm, until the sensor level index signal exceeds six. When the sensor indicated rate signal exceeds six, then the sensor-indicated rate signal assumes a value corresponding to the selected slope, reaction time, and recovery time characteristics.

Further, one aspect of the present invention relates to a method, used within or by a rate-responsive pacemaker as above described, of automatically setting a rate response threshold about which patient activity must rise before the rate-responsive functions become operable. This method includes the steps of subjecting the pacemaker to a known level of activity for a prescribed period of time, sampling and processing the sensor signals over the prescribed period of time to determine a representative sensor signal, adding a selectable offset value to the representative sensor signal, and using the value thus computed as the rate response threshold value.

DESCRIPTION OF THE DRAWINGS

These and other advantages of the present invention are best understood with reference to the drawings, in which:

FIG. 3 illustrates a preferred family of transfer curves used with the present invention in order to provide a selection of different slopes;

FIG. 7 is a first cutaway view of the rate-responsive pacer of FIG. 6;

FIG. 8 is a second cutaway view of the rate-responsive pacer of FIG. 6;

FIG. 10 shows a representative sensor-indicated rate histogram obtained from the pacer of FIG. 6;

DETAILED DESCRIPTION OF THE PREFERRED EMBODIMENT

The preferred embodiment of the present invention is contained in the following description for practicing the present invention. This description is not to be taken in a limiting sense but is made merely for the purpose of describing the general principles of the invention. The scope of the invention should be ascertained with reference to the appended claims.

Figure 1:
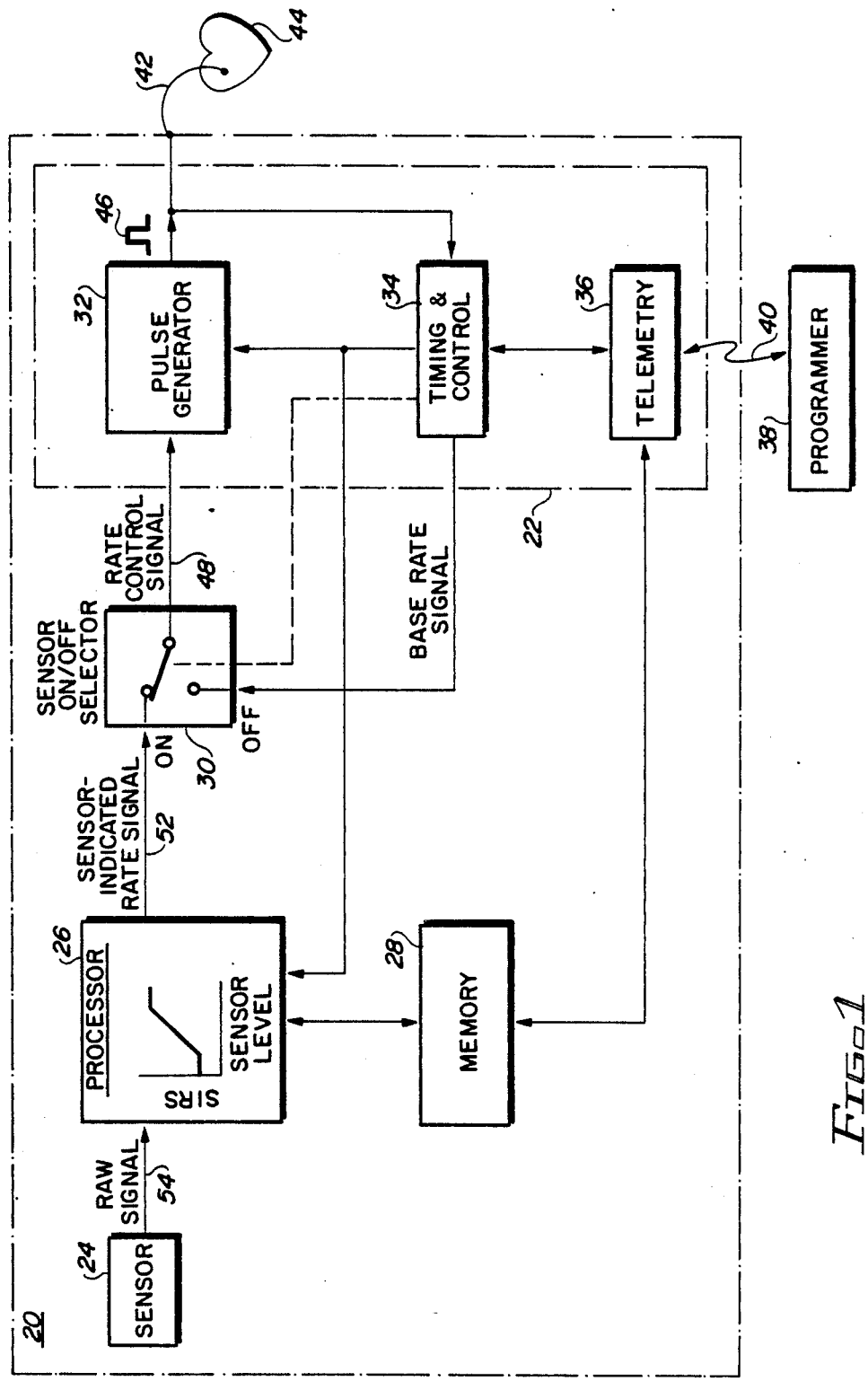
FIG. 1 is a functional block diagram of a rate-responsive pacemaker incorporating the features of the present invention.
Figure 11:
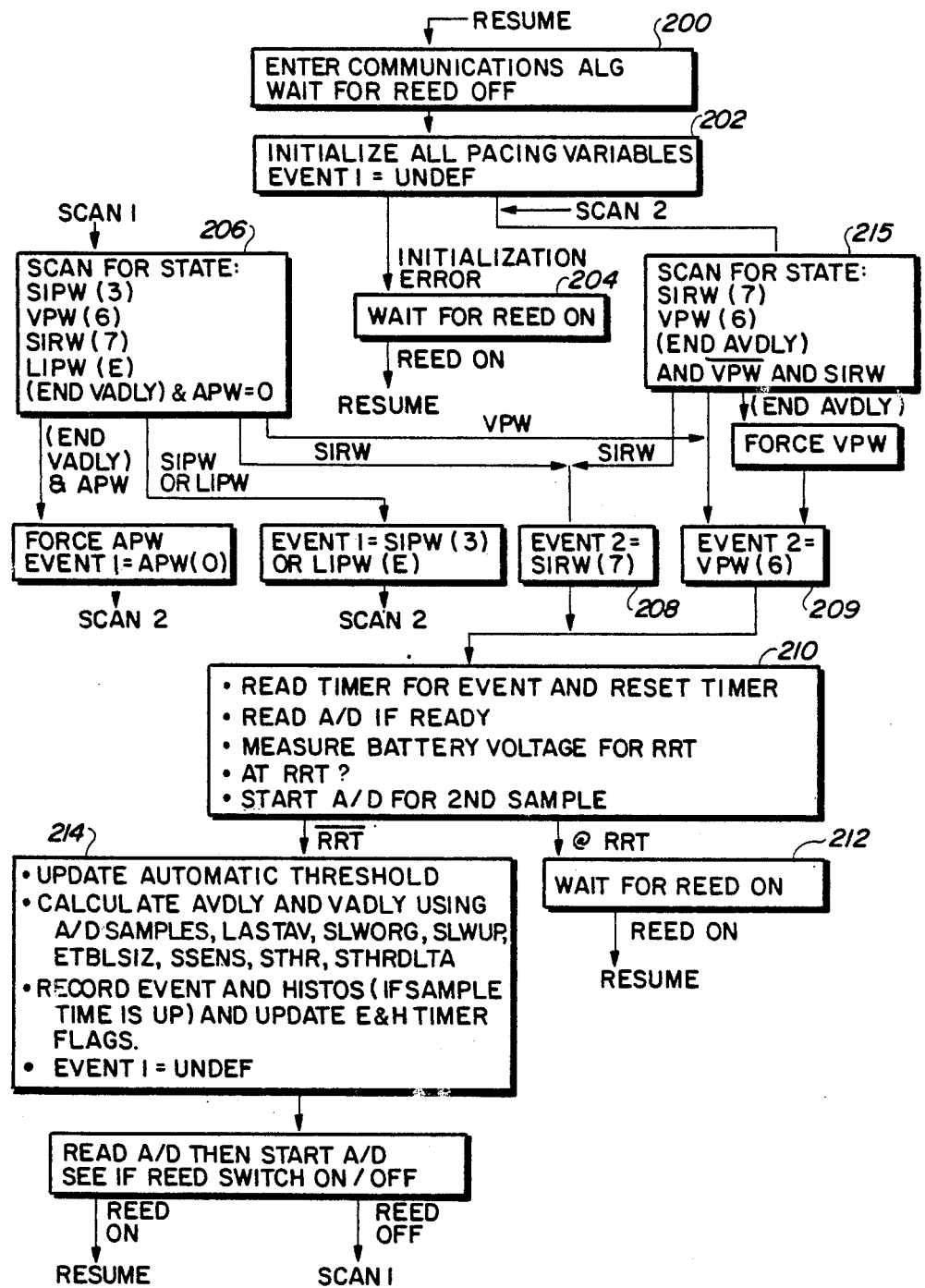
FIG. 11 is a flow chart of the rate-responsive pacing algorithm used by the pacer of FIG. 6.

As an outline and overview of the description which follows, a functional description of one embodiment of the rate-responsive pacer will first be presented in FIG. 1. This functional description is used to teach the basic operating principles of the invention, including the various programmable and automatic control parameters which may be used therewith, such as slope, rate response threshold, reaction time and recovery time (shown in FIGS. 2 through 5). Further, this functional description lays the foundation for the more hardware-oriented device description which is later presented (FIGS. 6-9). A description of the type of histogram data and event record which may be retrieved from the pacer will then be presented (FIG. 10), followed by a description of the rate-responsive algorithm used in the preferred embodiment (FIG. 11).

Referring first to the functional block diagram of FIG. 1, a rate-responsive pacemaker 20 configured in accordance with the teachings of the present invention is shown. The pacemaker 20 includes a conventional pacemaker chip 22, a sensor 24, a processor 26, memory circuit 28, and a selection means 30. The conventional pacemaker chip 22 includes at least a pulse generator 32, timing and control circuits 34, and telemetry circuits 36.

The pulse generator 32 includes at least one lead 42 which provides an electrical contact with the patient's heart 44. An external programmer 38 is also used to send programming signals to the telemetry circuits 36. These programming signals are depicted symbolically as the wavy line 40 in FIG. 1. It is noted that such signals may be sent either from the programmer 38 to the pacemaker 20, or from the pacemaker 20 to the programmer 38.

Functionally, the pulse generator generates stimulation pulses 46 at a rate determined by a rate control signal, appearing on signal line 48. These pulses, in turn, are delivered to the heart 44 through the lead 42 in conventional manner. This lead 42 may be either a unipolar lead, bipolar lead, or other multi-pole lead, all of which are known in the art. Further, although the sensor 24 is shown in FIG. 1 as being included within the pacemaker 20, it is to be understood that the sensor 24 could also be included within, or coupled to, the lead 42; or otherwise placed externally to the pacemaker 20.

The lead 42 also presents electrical signals occurring within the heart 44, such as P-waves and R-waves (evidencing natural cardiac activity of the atria and ventricles, respectively), to the timing and control circuits 34 and processor 26. Hence, for example, when programmed in a demand mode of operation, the pacemaker 22 is able to inhibit the generation of a pacing pulse 46 when natural cardiac activity is sensed within a designated time period, in conventional manner.

A more complete description of the pacemaker chip 22 and its operation may be found in several patents. For example, note U.S. Pat. No. 4,232,679, entitled "Programmable Human Tissue Stimulator," U.S. Pat. No. 4,686,988, entitled "Pacemaker System and Method for Measuring and Monitoring Cardiac Activity and for Determining and Maintaining Capture," and U.S. Pat. No. 4,712,555, entitled "Physiologically Responsive Pacemaker and Method of Adjusting the Pacing Interval Thereof." While not disclosing the exact same chip 22 or circuits which are used in the preferred embodiment of the present invention, these patents nonetheless disclose the primary components of a conventional pacing system and teach the basic operation thereof. U.S. Pat. Nos. 4,232,679, 4,686,988 and 4,712,555 are hereby incorporated herein by reference.

In operation, the rate-responsive pacer 20 may operate in either a SENSOR ON mode or a SENSOR OFF mode. The selection of a desired mode of operation is controlled by the selector 30, shown functionally in FIG. 1 as a switch. The selector 30 connects either a base rate signal on line 50 or a sensor-indicated rate signal on line 52 to the rate control signal line 48 of the pulse generator 32. Control of the selector 30 is obtained from the timing and control circuits 34, which control can be selected by an appropriate programming signal received from the programmer 38.

When the SENSOR OFF mode is selected, the selector 30 directs the base rate signal, generated by the timing and control circuits 34, to be the rate control signal line 48 of the pulse generator 32. This base rate signal thus controls the pacing rate of the pacer 20 in conventional manner.

Typically, the rate control signal 48 may be thought of as simply a signal responsible for generating a trigger pulse at the timing out of an escape interval (also generated by the timing and control circuits 34). However, if natural cardiac activity is sensed during the escape interval, no trigger pulse is generated by the pulse generator 32 and the timing circuits responsible for generating the escape interval are reset, thereby starting a new escape interval. Hence, regardless of the source of the rate control signal 48 (either the base rate signal 50 or the sensor-indicated rate signal 52), such signal may be overridden (if the pacemaker 20 is so programmed) by the sensing of natural cardiac activity.

When the SENSOR ON mode is selected, the rate control signal 48 of the pulse generator 32 is connected by way of the selector 30 to the sensor-indicated rate signal line 52 obtained from the output of the processor 26. The sensor-indicated rate signal is derived from a raw signal obtained from the sensor 24. Typically, the processor 26 includes means for converting the raw signal, appearing on signal line 54, to a sensor level index signal. This conversion may be accomplished in various ways, and in the preferred embodiment a transfer characteristic is used to convert the sensor level index signal to an appropriate sensor-indicated rate signal. The desired transfer characteristic may be stored or programmed into the memory 28 and used by the processor 26 to effectuate the conversion.

For an initial explanation of the rate-responsive transfer curve and the various parameters which may be adjusted thereon, reference is made to concurrently filed copending U.S. patent application Ser. No. 301,935, entitled "Energy Controlled Rate-Responsive Pacemaker Having Automatically Adjustable Control Parameters," which is assigned to the same assignee as is the present application, which copending patent application is hereby incorporated herein by reference.

Figure 12:
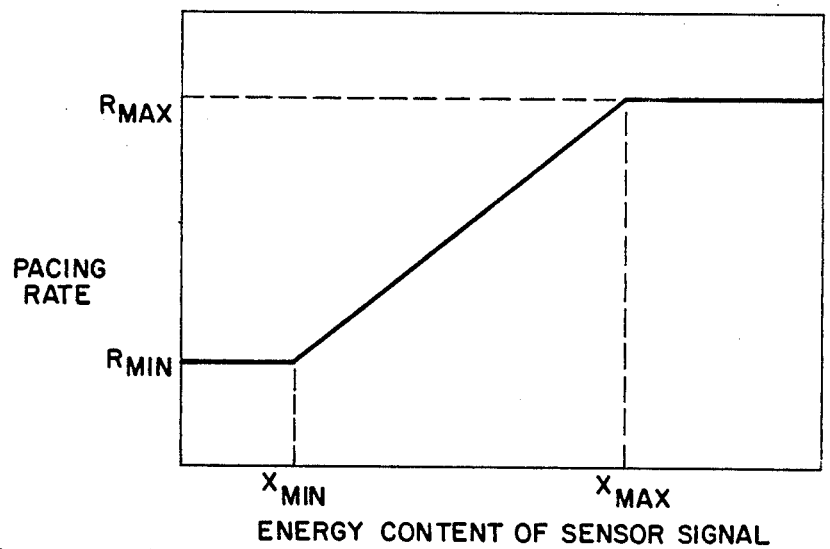
FIG. 12 shows a representative transfer curve of a rate-responsive pacemaker.

FIG. 7 of this above-referenced application is particularly relevant, and is reproduced herein as FIG. 12. Referring briefly to FIG. 12, the transfer characteristics of a typical rate responsive pacemaker are shown. The vertical axis of FIG. 12 represents the pacing rate, identified as R, while the horizontal axis represents the energy content of the raw signal from the sensor 12, identified as X.

As indicated in FIG. 12, there are four points on the transfer curve which significantly influence the operation of the pacemaker. These points include the minimum pacing rate, $R_{min}$, and the maximum pacing rate, $R_{max}$. The pacemaker, as controlled by the timing and control logic 34 and/or the processor 26, operates at the minimum pacing rate, $R_{min}$, so long as the energy content of the sensor signal remains below a minimum value, $X_{min}$. Similarly, the pacemaker operates at the maximum pacing rate, $R_{max}$, so long the energy content of the sensor signal remains above a maximum value, $X_{max}$.

If, however, the energy content of the sensor signal lies between $X_{min}$ and $X_{max}$, the pacing rate will vary as a function of the energy content of the raw signal according to a prescribed relationship. This prescribed relationship is depicted in FIG. 12 as a linear relationship. It should be noted, however, that any desired relationship, not just a linear relationship, could be used to relate the energy content of the raw signal from the sensor 24 to the pacing rate between the $R_{min}$ and $R_{max}$ points.

Still referring to FIG. 12, it may be noted that this transfer operation of transferring or converting the sensed energy content from the physiological signal (for example, the raw signal 54 from the sensor 24) to a pacing rate may be achieved by those skilled in the art in a variety of ways. For example, the transfer operation may be achieved within the processing circuits 26 and/or the timing and control logic 34 either algorithmically or by table look-up, as described above.

Figure 2:
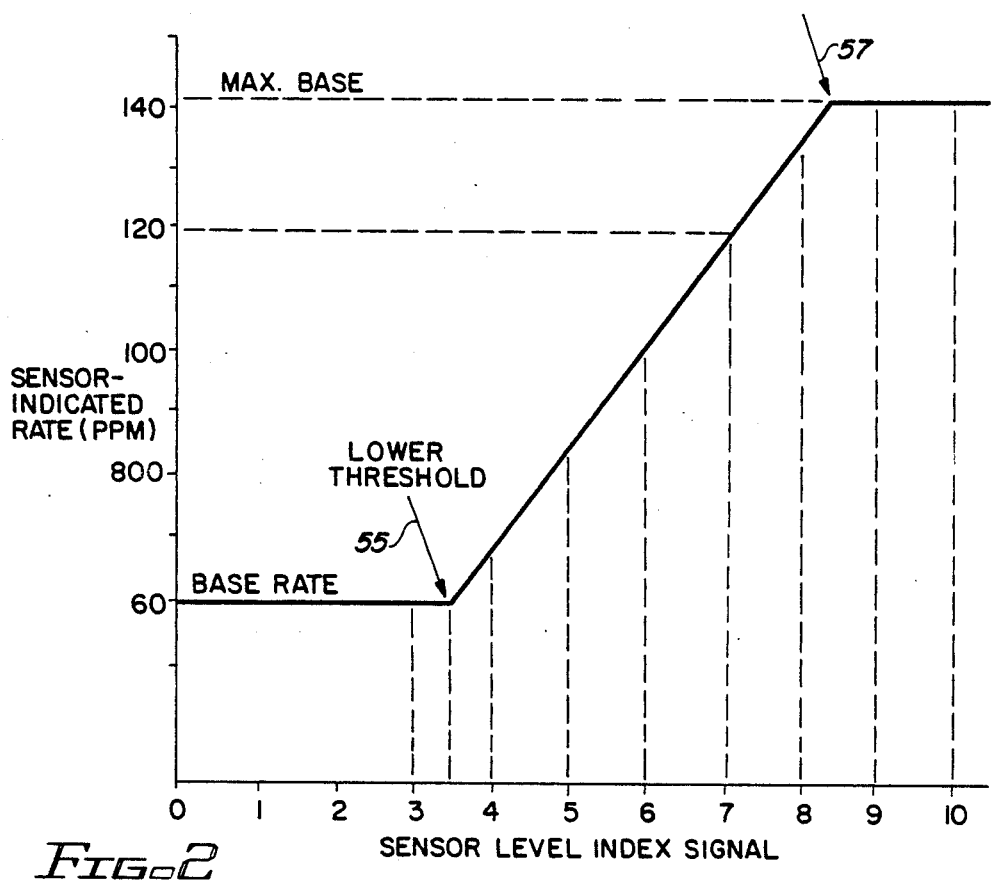
FIG. 2 is a transfer curve illustrating the general relationship between a sensor index signal and a sensor-indicated rate signal.

Referring next to FIG. 2, a typical transfer characteristic of a rate-responsive pacer is illustrated. As drawn, the vertical axis represents the pacing rate, or for purposes of this application, the sensor-indicated rate signal (SIRS). The horizontal axis represents a particular sensed parameter, or combination of sensed parameters, used to control the pacemaker. For purposes of this application, the horizontal axis is divided into equal increments, corresponding to different levels of energy (or other chosen parameter) associated with the raw signal 54 obtained from the sensor 24. These increments are identified as "sensor level index signals." It is believed that most applications would require at least ten index levels, as shown in FIG. 2, but certainly as few as four index levels could be used and still provide some measure of physiological control of the pacer.

In one embodiment, each increment of the sensor level index signal represents a uniform fractional increase of the energy content of the raw sensor signal. Thus, if ten index level signals are used, a sensor level index signal of 1 represents that the raw sensor signal contains 1/10 of its maximum possible energy, a sensor level index signal of 2 represents an energy content of 2/10 of the maximum possible energy, and so on. In another embodiment or variation of this feature, the energy content of the raw signal is effectively divided into energy zones, which zones may or may not represent equal amounts of energy. Each incremental sensor level index signal is assigned to a particular zone. Thus, if the energy content of the raw signal is determined to fall into zone 3, for example, the sensor level index signal is assigned a value of 3.

It is seen that the pacing rate indicated by the particular transfer relationship shown in FIG. 2 for any sensor index less than three is fixed at 60 ppm. This minimum pacing rate is referred to hereinafter as the "base rate." The sensor level index value below which the sensor-indicated rate signal does not change is referred to as the "lower sensor level rate response threshold", "lower rate response threshold", or sometimes simply "rate response threshold." This lower rate response threshold is identified in FIG. 2 by the reference numeral 55. As shown in FIG. 2, the lower rate response threshold has a sensor level index value of about 3.5. However, where only discrete values of the sensor level index signal are employed, as in a digital system, the sensor level index rate response threshold is effectively three. That is, for index levels three or below, the sensor-indicated rate signal is fixed at the base rate, shown in FIG. 2 as 60 ppm (although any desired base rate could be programmably selected).

Still referring to FIG. 2, it may be seen that index levels having a value of four through eight define a sensor-indicated rate signal that varies as a function of the transfer curve. For example, a sensor index of seven in FIG. 2 defines a sensor-indicated rate signal of 120 ppm. Sensor level index signals in excess of nine define a maximum rate for the pacer. The point at which this maximum rate begins is identified in FIG. 2 by the reference numeral 57. This point may be referred to as the "maximum rate response level." For the example shown in FIG. 2, the maximum rate response level has an effective value of nine (assuming discrete index level signals).

Referring next to FIG. 3, a family of sixteen different transfer curves for use with a preferred embodiment of the present invention is shown. The horizontal axis of FIG. 3 is labeled "Relative Sensor Level Index Signal". This horizontal axis corresponds roughly to the sensor level index signal described above with reference to FIG. 2. However, in the preferred embodiment shown in FIG. 3, thirty-two relative sensor index signal increments, identified by the integers 0–31, are used to represent the area in FIG. 2 from the lower threshold point 57 to the maximum sensor level index signal.

In this case, a relative sensor level index signal of zero in FIG. 3 corresponds to the lower threshold point 57 of FIG. 2, and thus the prefix "relative" is added to the term sensor level index signal. However, more or less than thirty-two levels could be selected depending upon the particular sensitivity desired relative to changes in the raw signal from the sensor 24. The vertical axis of FIG. 3 is identified as the "Relative Pacing Rate." This vertical axis is a relative representation of the sensor-indicated rate signal described above with reference to FIG. 2.

As defined in FIG. 3, relative pacing rates of from 0 to 105 ppm are shown. These relative values are added to the base rate or programmed rate of the pacer. For example, if the base rate is programmed to be 60 ppm, and if the relative sensor level (index signal) is ten, and if curve number 9 is chosen as the defining curve, then the relative pacing rate is 40 ppm. This means that the maximum sensor-indicated rate signal would be 100 ppm (the base rate plus the relative rate: 60 ppm+40 ppm=100 ppm).

The particular curve of the family of curves which is selected for any given patient is selected by programming a parameter termed "slope". The programmed slope value determines the increase in pacing rate (above the programmed base rate) which will occur at various levels of patient activity.

Patient activity is detected by the sensor 24 (FIG. 1). In the preferred embodiment, as has been indicated, the sensor 24 is a piezoelectric transducer bonded to the inside of the pulse generator enclosure. The raw signal 54 generated by this transducer is processed by the processor 26 and converted to the sensor level index signal. The energy level of the raw signal is measured and is used as the basis for determining the appropriate sensor level index signal.

Reference should be made to the aforementioned patent application entitled "Energy Controlled Rate-Responsive Pacemaker Having Automatically Adjustable Control Parameters" for further details associated with the manner in which the raw signal from the piezoelectric sensor is processed. In operation, once the energy content of the signal has been determined and converted to a raw digital sensor level index signal, a programmed rate response threshold value is subtracted from the raw digital sensor level index signal to obtain the relative sensor level index signal. The relative sensor level index signal may assume a discrete value from 0 to 31, and may be thought of as the amount by which the raw sensor level (i.e., the energy content of the raw sensor signal) exceeds the programmed rate response threshold.

The sensor level index signal advantageously provides a measure of the activity or other physiological parameter of the patient. In general, low sensor level index signals correspond to low levels of patient activity whereas maximum sensor level index signals correspond to high levels of activity. As illustrated in FIG. 3, there are sixteen programmable slope values which define the increases in pacing rate which occur for all possible sensor level index signals. Higher slopes result in a greater increase in pacing rate than do lower slopes for any specific sensor index (level of patient activity). Thus, by selecting an appropriate slope, the response of the pacer to a particular level of patient activity may be customized to suit the individual needs of a particular patient.

In order to prevent inappropriate increases in pacing rate while the patient is at rest or at low levels of activity, the rate-responsive pacer of the present invention offers a plurality of programmable rate response threshold values which may be selected. In general, as described above in connection with FIG. 2, "rate response threshold" may be thought of as that sensor level which must be exceeded before the rate-responsive functions of the pacer take effect. That is, for sensor levels below the rate response threshold, the sensor indicated rate signal remains fixed at the base rate (meaning that the relative sensor-indicated rate signal is zero).

In order to provide a programmable rate response threshold, an "offset" value is used. Offset is that value which is subtracted from the raw sensor level index signal prior to converting it to the final sensor level index signal. Conceptually, offset is like a bias signal which is subtracted from the raw sensor signal level in order to effectively shift the break point of the transfer curve in a desired direction. Use of an offset value in this manner to set a rate response threshold value thus defines a selectable minimum level of patient activity which must occur before the sensor indicated pacing rate increases above the programmed base rate.

More particularly, the raw sensor signal for the pacer of the present invention is an analog signal having a wide and varied amplitude and frequency associated therewith. This signal is rectified and filtered, providing an analog signal level that varies as a function of the energy content of the raw signal. The method of rectification may be full wave rectification or half wave rectification, or alternately half wave rectification using a level other than zero. This analog signal is then converted to an appropriate digital raw sensor level signal.

A rate response threshold value of, for example, between one and seven may then be selected. When a particular rate response threshold value is selected, a corresponding offset value is subtracted from the digitized raw sensor level signal, resulting in the sensor level index signal previously described.

Figure 4A:
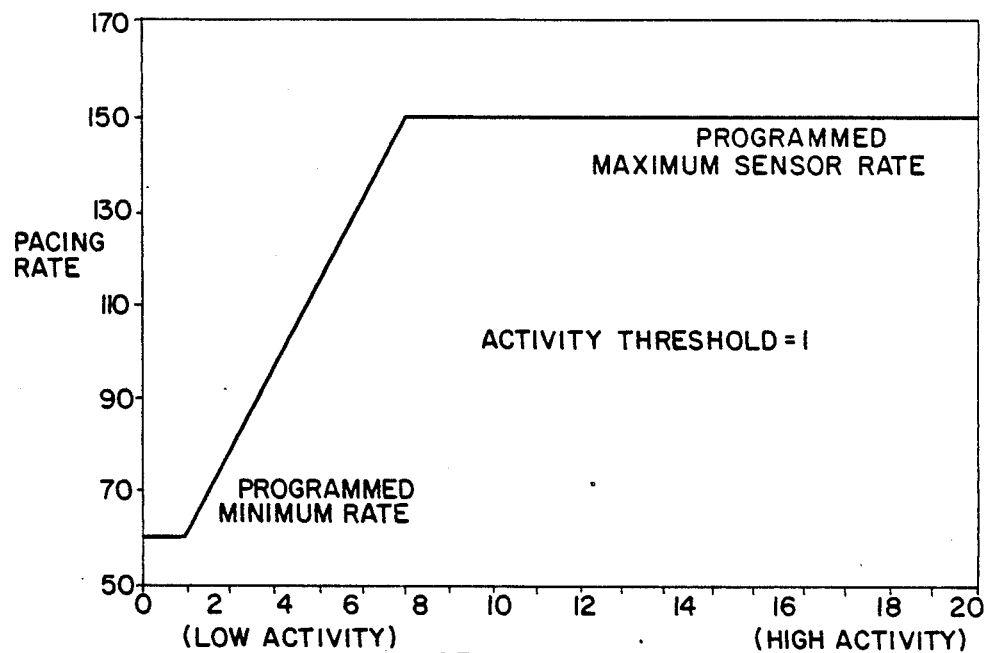
FIG. 4A is a first transfer curve used to teach the concept of a programmable and automatic rate response threshold.
Figure 4B:
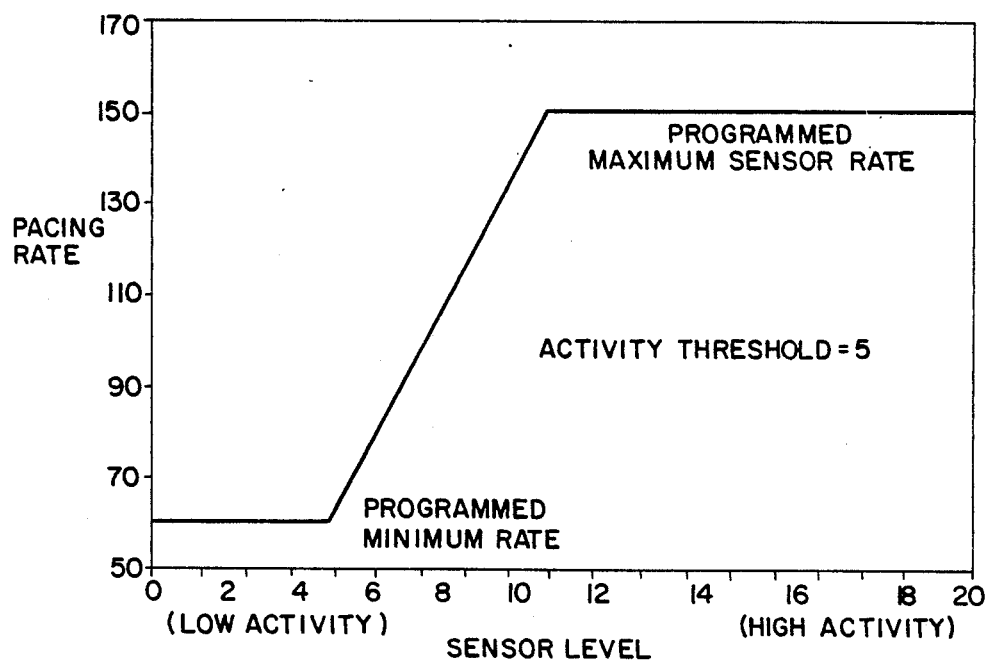
FIG. 4B is a second transfer curve used to teach the concept of a programmable and automatic rate response threshold.

The effect of selecting a low or high rate response threshold value is illustrated in FIGS. 4A and 4B, respectively. At a rate response threshold of 1, for example, the transfer relationship shown in FIG. 4A effectively results. This particular relationship allows increases in pacing rate to be observed at fairly low levels of patient activity. For example, a digitized raw sensor level signal of two or higher allows the pacing rate to increase. However, if a rate response threshold of five is selected, as shown in FIG. 4B, a much higher level of patient activity is required before an increase in pacing rate is observed (digitized raw sensor level signals of six or greater are needed).

Advantageously, the present invention also provides for the automatic setting of the rate response threshold. This "autothreshold" feature eliminates the need to manually select activity rate response threshold. When the autothreshold feature is selected, the activity rate response threshold at any particular point in time is determined by the processor 26 (FIG. 1) by adding the average sensor level index signal over a prescribed prior period of time to a prescribed rate response threshold offset value. In the preferred embodiment, the prescribed prior period of time is the preceding 18 hours, and the prescribed rate response threshold offset is two (2).

Other measures of the sensor level index signal, in addition to, or in place of, an average index signal, could also be used. For example, a weighted average of the index signals could be performed, giving greater weight to the index signals from certain time periods of the day. Further, a least squares computation could be performed wherein index values having a large variance from other index values are discounted. In other words, any processing method or technique that provides a meaningful measure of the variation and movement of the sensor index over the time period of interest may be used. This measure of movement may be thought of as a type of reference sensor signal representative of all, or most all, sensor signals occurring during the desired time period. An average is used in the preferred embodiment because an average may be easily determined.

The autothreshold feature advantageously recognizes that nearly all patients will be at a relatively low level of activity for most of any 18 hour period. The memory circuits 28 (FIG. 1) thus continuously record the average sensor level for the prior 18 hour period (or other prescribed time period). This running average is continuously updated with new sensor levels that are measured every pacing cycle. Each reading of the individual sensor has only a small effect on the average because of the large number of pacing cycles which occur in an 18 hour period.

As an example of the autothreshold feature of the present invention, assume that the prescribed period of time over which the sensor level index signal is averaged is eighteen hours and that the prescribed rate response threshold offset is two. If the average sensor level index signal for the preceding 18 hours is one, then the rate response threshold offset is automatically set to be three (the 18 hour average of one added to the prescribed offset of two).

Figure 5A:
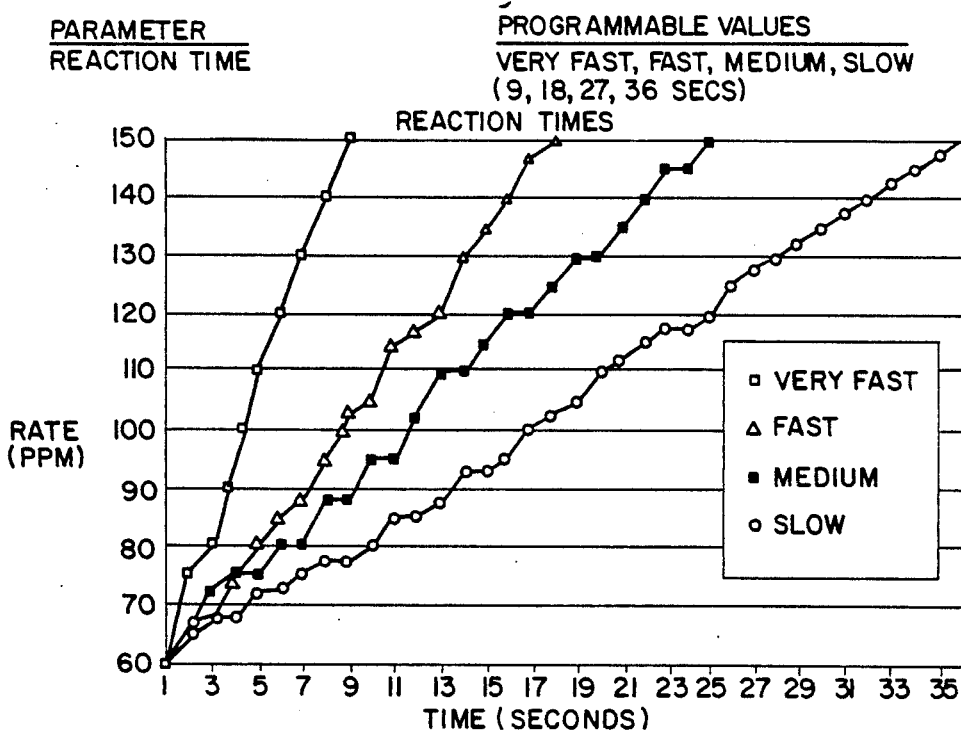
FIG. 5A is a graph which illustrates the various reaction times used with the present invention.

Referring next to FIG. 5A, the concept of reaction time is presented. Reaction time is the minimum time allowed for an increase in pacing rate from the programmed basic rate to the maximum sensor-indicated rate. A short reaction time allows the pacing rate to increase rapidly in response to patient activity, whereas a long reaction time forces a slow increase in pacing rate. As seen in FIG. 5A, four programmable reaction times are provided in the preferred embodiment of the invention. More or less than this number of reaction times could, of course, also be included.

These programmable reaction times are identified as "very fast," "fast," "medium," and "slow." FIG. 5A illustrates the change in pacing rate versus time in response to a sudden increase to maximum activity level for the four programmable reaction times. It is noted that the programmed reaction time only applies to increases in pacing rate resulting from sensor detected activity. Reaction time has no effect when the pacemaker is operating in a non-rate-responsive mode.

Figure 5B:
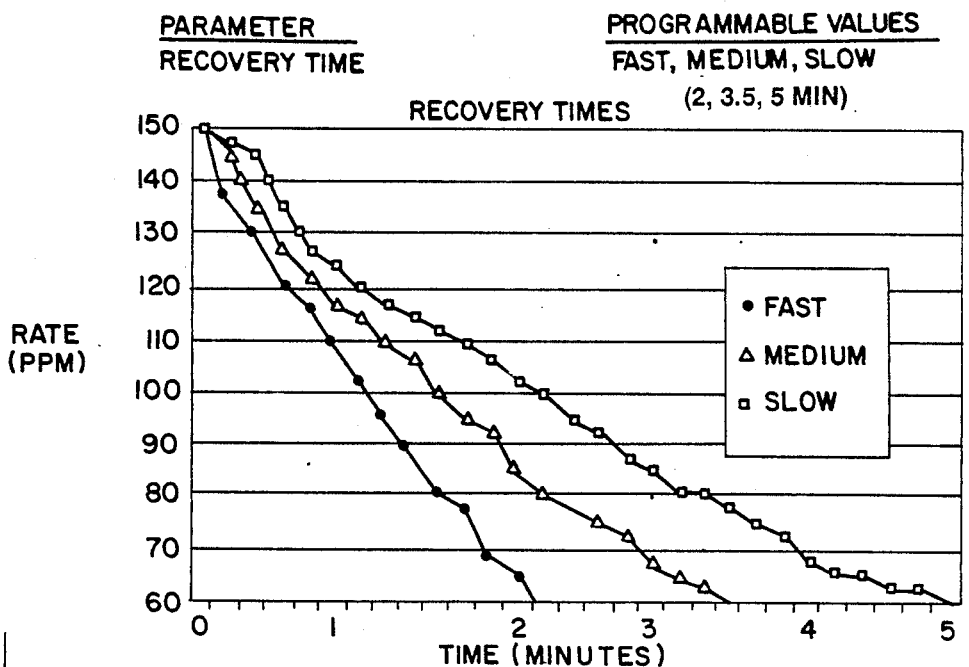
FIG. 5B is a graph which shows the recovery times used with the pacer of the present invention.

Similar to the concept of reaction time is "recovery time." Recovery time determines the minimum time required for a decrease in the pacing rate from the maximum sensor-indicated rate to the programmed basic rate. This feature advantageously prevents abrupt decreases in pacing rate concurrent with the conclusion of sensed patient activity. As shown in FIG. 5B, there are three values of recovery time which may be programmably selected in the preferred embodiment of the invention: fast, medium and slow.

A long or slow reaction time results in a slow decrease in pacing rate when the patient's activity level decreases. A short or fast reaction time allows the pacing rate to decrease more rapidly. FIG. 5B illustrates changes in the pacing rate versus time in response to a sudden decrease in activity for each of the three programmable recovery times. As with reaction times, the set recovery times apply only to decreases in pacing rate resulting from sensor detected activity. The recovery time selected will not affect pacing rate when the pacemaker is operating in a non-rate-responsive mode, such as during tracking or triggered operation.

Figure 6:
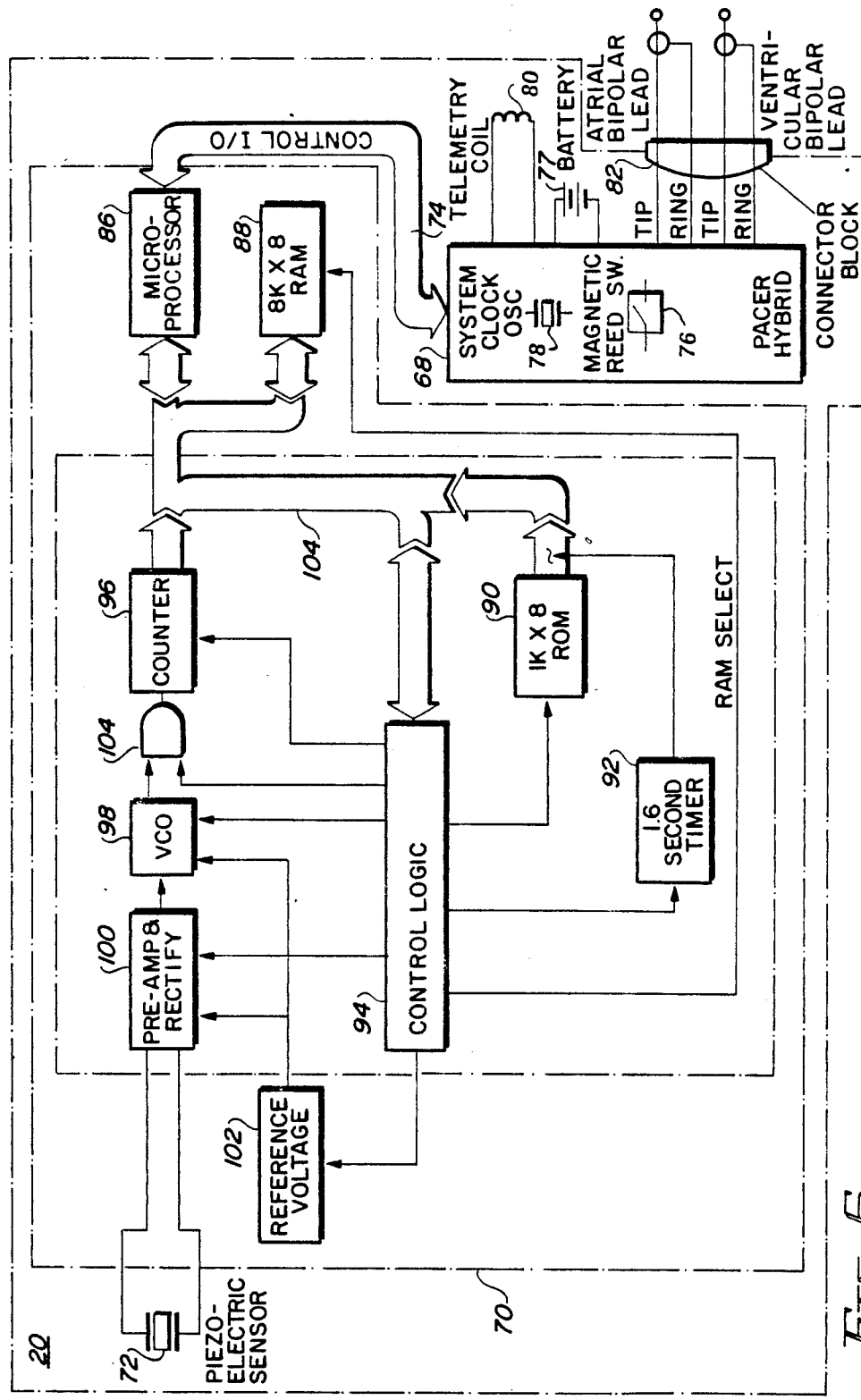
FIG. 6 is a block diagram of the preferred embodiment of a rate-responsive pacemaker configured in accordance with the teachings of the present invention.

Referring next to FIG. 6, a block diagram of a preferred embodiment of the rate-responsive pacer 20 of the present invention is shown. FIG. 6 differs from FIG. 1 in that FIG. 1 is a functional block diagram, whereas FIG. 6 is more of a hardware block diagram. However, as may be seen by a comparison of the two figures, many of the components of the two diagrams are the same or similar (although in the two figures the components do not share common reference numerals).

As seen in FIG. 6, the pacer 20 includes a conventional pacer hybrid circuit 68 and a microprocessor rate-responsive hybrid circuit 70. Also included in the pacer is a piezoelectric sensor 72 which is connected to the microprocessor hybrid circuit 70. The only electrical connections between the pacer hybrid circuit 68 and the microprocessor hybrid circuit 70 are an I/O bus 74 and power and ground connections (not shown). Included within the pacer hybrid circuit 68 are conventional pacer components, such as a magnetic reed switch 76 and a system clock oscillator 78. Also included in the pacer 20 are a telemetry coil 80, a connector block 82 to which industry-standard pacing leads may be connected, and a battery 77.

The preferred manner in which the above-enumerated components, as well as the sensor 72 and the microprocessor hybrid circuit 70 are packaged within a suitable enclosure or case 84 is illustrated in the cutaway views of FIGS. 7 and 8. FIG. 7 comprises a perspective cutaway view while FIG. 8 comprises an end cutaway view. As seen in these figures, the pacer hybrid circuit 68 and the microprocessor hybrid circuit 70 are placed side by side above the battery 77. The piezoelectric sensor 72 is bonded to the case 84 so as to detect any pressure applied to the case 84 (such as that which occurs when the patient engages in physical activity).

Referring again to FIG. 6, the microprocessor hybrid circuit 70 includes a microprocessor circuit 86 which is electrically connected to the I/O bus 74. A flex cable 75 (FIG. 8) is used to connect the battery 77, the connector block 82, and the pacer hybrid circuit 68. Also included as part of the microprocessor hybrid circuit 70, as shown in FIG. 6, are a random access memory (RAM) 88, a read only memory (ROM) 90, a timer circuit 92, a control logic circuit 94, a counter 96, a voltage controlled oscillator (VCO) 98, a preamplifier and rectifying circuit 100, a reference voltage circuit 102, and a functional AND gate 104.

All of these components cooperate to produce a digital signal representative of the energy content of the raw signal obtained from the piezoelectric sensor 72 in a manner the same as, or substantially similar to, that described in the above-referenced copending patent application. Reference should be made to that application, especially to FIG. 6 thereof and the accompanying text, for a description of the manner in which the index signal may be generated.

Basically, the raw signal from the sensor 72 is amplified and rectified and filtered in the preamplifier and rectifying circuit 100. The resulting analog signal drives the VCO 98, the output of which is counted in the counter 96 for a prescribed period of time (the sample time), set by the timer circuit 92. At the end of the counting period, the final count held in the counter 96 is thus representative of the frequency variations of the VCO 98, which variations, in turn, are representative of the energy content of the raw sensor signal.

Hence, the count held in the counter 96 provides a digital signal which represents the energy content of the raw signal. This digital signal may then be transferred to either the microprocessor 86 for further processing, or to the RAM 88 for storage, over the data/control bus 104. The data/control bus 104 interconnects the counter 96, the control logic circuit 94, the ROM 90, the timer circuit 92, the RAM 88 and the microprocessor 86.

The case 84 in which the components as above described are housed is preferably made from titanium coated with a bio-compatible insulting material on all but one side. This exposed side functions as a return electrode for any unipolar modes of operation which may be selected.

The battery 77 may be a lithium-iodine battery model 8074, which is manufactured by Wilson Greatbatch Company. This battery provides 2.3 ampere hours of usable energy at nominal pacing conditions (dual bipolar operation, 70 ppm, standard parameters, and 100% pacing).

The ROM 90 may be a 1K×8 bit read only memory which contains the basic program used to load desired software into the on-board RAM 88. The RAM 88 may be an 8K×8 bit CMOS device which provides the needed storage space for the desired software. The microprocessor 86 may be a MC146805 CMOS Static Microprocessor manufactured by Motorola. It is the control center for implementation of the desired software.

The software stored in the RAM 88 is utilized by the microprocessor 86 to: (1) perform sensor-data acquisition and to generate the sensor-indicated rate signal from the signal held in the counter 96 at the sample time; (2) control the pacer hybrid circuit 68 (for the SENSOR ON Mode); (3) perform data transfers between the RAM 88, the control logic 94, and the I/O bus 74 for monitoring and control of the various states of the pacer hybrid circuit 68; (4) compute running averages of the sensor index signal or other calculations needed or desired; and (5) perform whatever other tasks need to be done for a particular application as directed by the controlling software. Inasmuch as a commercially available microprocessor is used for the processor 86, the operation and use of which is well documented in the art, those skilled in the art could readily provide the necessary programs for accomplishing the tasks described herein.

Figure 9:
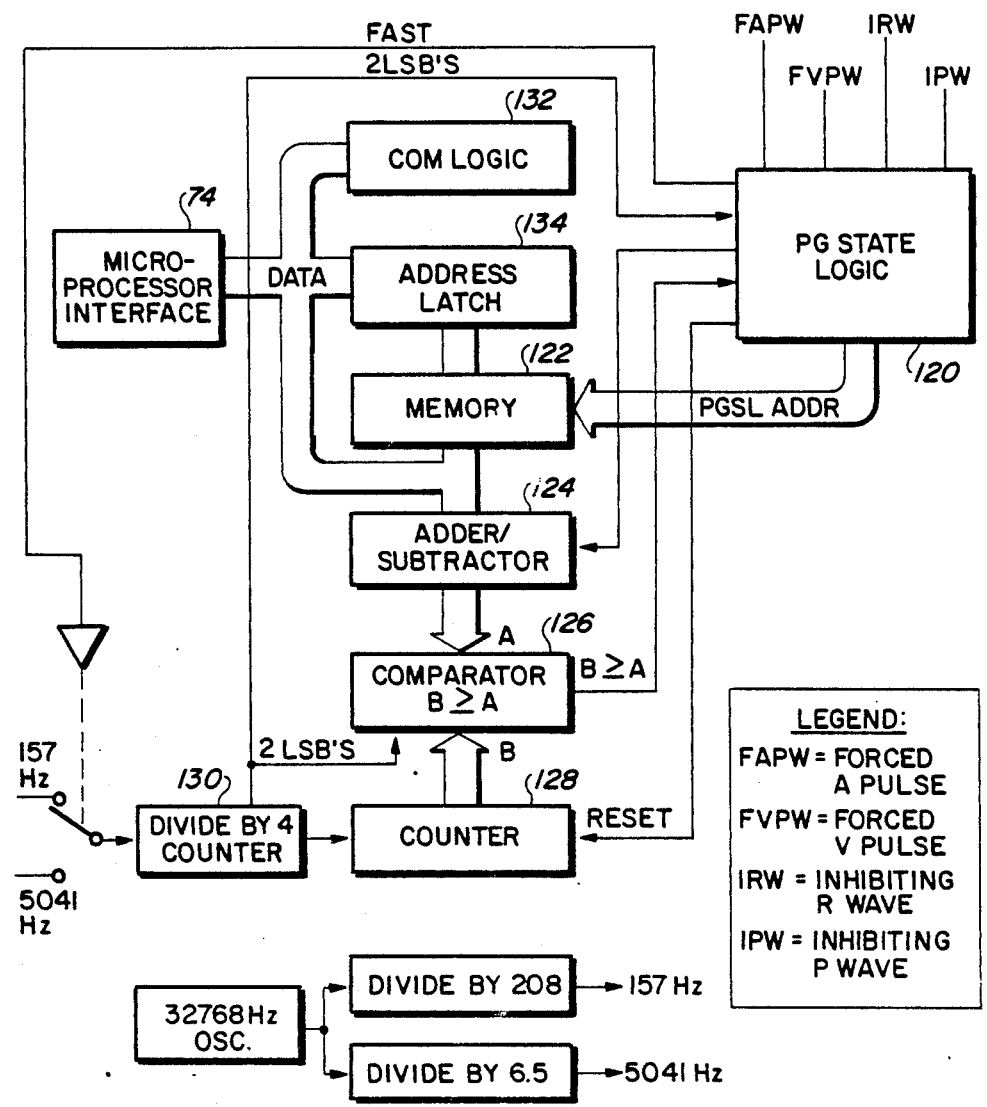
FIG. 9 is a block diagram of selected portions of the conventional pacer hybrid portion of FIG. 6.

Referring next to FIG. 9, a block diagram of selected portions of the pacer hybrid circuit 68 is shown. The pacer hybrid circuit operates on the state machine principle where all events of the pacer are based on a Pulse Generator (PG) state logic 4-bit register 120. The state of the PG state logic 120 is determined by a state timer and/or by sensed cardiac events. As various sensed events occur, and/or as various time intervals expire, the state of the PG state logic 120 thus cycles through different states.

The concept of a state machine as applied to a pacemaker is explained more fully in U.S. Pat. No. 4,712,555, which patent has been incorporated herein by reference above. FIGS. 14A-14C and FIG. 15 of this referenced patent, and the accompanying text, illustrate state machine operation. For purposes of the present invention, it suffices to state that each pacing cycle is comprised of a plurality of states, each state initiating a specified time interval (such as a blanking interval, an absolute refractory period, or a V-A delay), some of which intervals may be reset in the event a sensed cardiac event occurs.

The occurrence of some states is common to all pacing cycles. The occurrence of other states depend upon the particular programmed mode of operation of the pacer and/or the particular cardiac events which are sensed. Hence, it is a relatively simple matter to define a pacing cycle (and to develop an appropriate sampling signal which occurs every pacing cycle) by monitoring the PG state logic 120. The occurrence of a common state, followed by the occurrence of at least one other state, followed by the reoccurrence of the same common state, thus signals that a cardiac cycle has been completed. Hence, by simply monitoring when one of these common states occurs, such as the V-A delay state (VAD), an indication is provided that a pacing cycle has occurred. The occurrence of a pacing cycle is important to the present invention because the sensor level index signal is typically generated once each pacing cycle.

Coupled to the PG state logic 120 is memory circuitry 122. The memory circuitry 122 has prescribed control signals stored therein at specified locations. These control signals are addressed by the state of the PG state logic 120. These control signals, once addressed by the PG state logic 120, may be further processed, such as by an adder/subtracter 124 and a comparator 126, and related circuitry (such as a counter 128, a divide circuit 130, and other circuits not illustrated herein), in order to bring about a desired event, such as the starting of a prescribed time interval. Once the prescribed event occurs, e.g. as the timing out of a particular time interval, or once a sensed cardiac event occurs, appropriate steering signals are feed back to the PG state logic 120 to cause the next appropriate state of the PG state logic 120 to be entered.

The PG state logic 120 states for the pacer hybrid circuit 68 are summarized in Table 1 below. The normal sequence for the FG state logic state machine in the absence of P or R waves or noise in any pacing mode is: 0, 1, 5, 4, 6, 2, A, B, 9, 8, C, 0.

TABLE 1

| State | Symbol | Description |
| --- | --- | --- |
| 0 | APW | A Pulse |
| 1 | BLANK | V Sense Input Inhibit (Blank) |
| 2 | AREF | A Refractory |
| 3 | SIPW | Sensed Inhibiting P Wave |
| 4 | AVD | A-V Delay |
| 5 | CROSS | Crosstalk Sense |
| 6 | VPW | V Pulse |
| 7 | SIRW | Sensed Inhibiting R Wave |
| 8 | VAD | V-A Delay |
| 9 | SHORT1 | Shorten A-V Delay 50 msec if IPW during SHORT1 with Physiologic A-V Delay On |
| A | MTR | Maximum Track Rate - Shorten A-V Delay 25/75 msec and Delay IPW until MTR end if P wave sensed during MTR; 75 msec if Physiologic A-V Delay On |
| B | SHORT2 | Shorten A-V Delay 75 msec if IPW during SHORT2 with Physiologic A-V Delay On |
| C | RRT | Lengthen V-A interval if at low battery |
| D | RNOISE | R Noise sensed during VREF or RNOISE |
| E | LIPW | Latched IPW - P wave sensed in MTR |
| F | PNOISE | P Noise sensed during AREF or PNOISE |
| (none) | VREF | V Refractory, independent 1-bit state machine synchronized to PGSL when AREF starts |
| (none) | ABSREF | 108 msec Absolute Refractory starts when AREF starts |

In addition to the PG state logic 120, various communication states may be set by the COM logic 132. The COM logic 132 determines the telemetry state of the pacer 20. The particular sequence of COM states depends on the type of telemetry command (memory, measured data, or interrogate) that is received from the external programmer 38 (FIG. 1). For purposes of the present invention, it is only significant to note that both the memory 122 and the COM logic 132, as well as the address latch 134, are coupled to the microprocessor interface bus 74.

Hence, data may be requested by and sent from the pacer hybrid circuit 68 to the microprocessor I/O hybrid circuit 70 (such data may include information received from the external programmer), or data may be received by the pacer hybrid circuit 68 from the microprocessor hybrid circuit 70 (which may include data or information which is to be sent to the external programmer). The details of the manner in which such data transfers may occur are known to those skilled in the art and will not be described further herein. Further, an understanding of such details are not believed to be critical to an understanding of the present invention.

Some of the data which may be sent from the microprocessor hybrid circuit 70 to the pacer hybrid circuit 68 includes the sensor-indicated rate signal sampled at an appropriate (and selectable) sampling interval. This signal may be stored within the memory circuits of the pacer 20 and later retrieved and sent to the external programmer 38, or an equivalent device, and displayed in a convenient histogram format.

FIG. 10 shows a representative histogram of the type which may be displayed. This histogram provides numeric and graphic representations of the sensor-indicated pacing rate distribution since the memory of the pacer was last cleared. This feature advantageously allows an assessment of the appropriateness of the programmed activity response parameters by providing the physician (or other medical personnel) with an easy mechanism for examining the sensor response to patient activities over both short and long periods of time.

In the preferred embodiment, the sampling rate for the histogram may be programmed to one sample every 1.6 seconds or one sample every 26 seconds. Even at the maximum sampling rate, the histogram memory is capable of storing data for a minimum of 310 days before reaching capacity and freezing the histogram memory.

It is noted that the sensor indicated rate histogram will not necessarily correspond to the actual pacing rate during the recording period. This is because if the natural rate of the heart always exceeds the sensor indicated rate, the pulse generator will be continuously inhibited. However, the histogram memory is still continuously updated with the pacing rate which would have been provided in the absence of natural activity. Further, the sensor indicated rate histogram may be selectively recorded even when the pacer is programmed to SENSOR OFF. In such an instance, the pacing rate that would have been provided in the absence of natural cardiac activity, and if the sensor had been programmed on, is continuously recorded.

This feature (of being able to record the sensor indicated rate even with the sensor programmed off) advantageously allows a determination to be made of the appropriate slope and rate response threshold values before the sensor is programmed on. This practice helps avoid inappropriate pacing rate variations which might occur if the sensor were programmed on before appropriate values were selected.

It is further noted that the programmer 38 (FIG. 1) includes means for displaying and printing any data received from the pacer 20, including the sensor-indicated rate histogram data as above described, as well as other useful data, such as event histogram data and event time records. Advantageously, this data may be printed or displayed in an easy to read and understand format, such as the sensor indicated rate histogram depicted in FIG. 10.

In operation, the following procedure may be utilized to select appropriate slope and rate response threshold values prior to programming the pulse generator to SENSOR ON:

1. Clear the pacer's histogram memory. Set the histogram sampling rate to 1.6 seconds. If use of the autothreshold setting for rate response threshold is desired, program the rate response threshold to "auto" at this time.
2. Engage the patient in a low level of activity (such as walking slowly) for approximately two minutes.
3. Read the sensor indicated rate histogram and generate a printout or other display. The printout should be labeled "low work."
4. If the "auto" rate response threshold setting has not been selected, examine the sensor indicated rate histogram and determine if the rate range with the highest percentage of samples corresponds to the desired pacing rate during a low level of activity. If it does not, the rate response threshold should be increased or decreased. In general, increasing the rate response threshold by one will decrease the pacing rate during a low level of activity by approximately 5 ppm. Decreasing the rate response threshold by one will increase the pacing rate by 5 ppm. Adjust the programmed rate response threshold using this general rule. For example, if the histogram shows that the sensor indicated rate during a low level of activity is 10 ppm faster than desired at a programmed rate response threshold of 4, the rate response threshold should be increased to 6.
5. Clear the histogram using the programmer. Maintain the sampling rate at 1.6 seconds.
6. Engage the patient in a high level of activity (such as a fast walk or jog) for approximately two minutes.
7. Read the sensor indicated rate histogram and generate a printout that is labeled "high work."
8. Examine the sensor indicated rate histogram and determine the rate range with the highest number of samples. If this corresponds to the desired pacing rate during high levels of activity, then the programmed slope is appropriate. If it does not, refer to the pacing rate versus sensor level graph (FIG. 3) to determine the appropriate slope. This figure is used by first identifying the point at which the rate during high levels of activity intersects the line corresponding to the programmed slope. This allows identification of the sensor level index which is achieved during a high level of activity. To find the appropriate slope, move up or down along the vertical line corresponding to this sensor level index until the horizontal line corresponding to the desired pacing rate during high levels of activity is reached. The slope line which lies nearest to this point should give the desired pacing rate increase during high levels of activity. Program the pulse generator to this slope line.

9. Repeat the evaluation at low and high activity levels (with histogram printouts) to verify the appropriateness of the slope and rate response threshold settings which have been selected.
10. Program the reaction time, recovery time and maximum sensor rate to the desired settings prior to programming the pulse generator to SENSOR ON.

An important feature included within the rate-responsive pacer of the present invention is the pacer's ability to operate independently of any of the rate-responsive functions in the event of a microprocessor or sensor failure. This feature goes beyond the programmable aspects included in the pacer, wherein the sensor may be programmed either on or off. Rather, this feature automatically causes the pacer to revert to a non-rate-responsive mode of operation, totally independent of any of the functions not included in the pacer hybrid circuit 68 (FIG. 6). As such, this feature is a form of fail-safe mechanism which guarantees that the pacer will always provide a life sustaining stimulation pulse when needed.

This fail-safe feature is achieved because of the demand-type operation of the pacer hybrid circuit 68. That is, the pulse generator and timing circuits 34 (FIG. 1) are configured to always provide a stimulation pulse within a safe time in the absence of natural cardiac activity (for certain modes), or every pacing cycle (for certain other modes), even if no signal is received from the microprocessor hybrid circuit 70.

Hence, if the microprocessor hybrid circuit 70 ceases to function for any reason, the pacer hybrid circuit 68 independently continues to assure that life sustaining pacing pulses are always delivered to the patient. Thus, the timing circuits of the pacer hybrid circuit 68 act as back-up control circuits to the control circuits of the microprocessor hybrid circuit 70 to ensure that a proper pacing function is always provided, even if it is not a rate-responsive function.

Next, reference is made to FIG. 11 wherein a flow chart of the rate-responsive pacing algorithm used with the present invention is shown. This flow chart is self explanatory when read in conjunction with Table 1, which Table provides a definition for many of the states identified in FIG. 11.

As seen in FIG. 11, when a programmed change is to be made to the pacer, the first step is to enter the communications algorithm (block 200), so that all pacing variables may be initialized (block 202). This requires that the reed switch 76 (FIG. 6) be on. If there is an initialization error, the algorithm waits until the reed switch is on again (block 204). Once pacing variables have been initialized, a pacer state scan, identified as Scan 2 (block 215), is initiated.

Depending upon the particular state which is sensed during this scan, various paths may be taken as indicated in FIG. 11. If the state SIRW (Sensed Inhibiting R Wave, see Table 1) is sensed, for example, then Event 2 is defined as an SIRW (State 7), (block 208), and control is passed to block 210. Similarly, if during Scan 1 the state sensed is VPW (V Pulse), then Event 2 is also defined as a VPW (State 6) (block 209), and control is passed to block 210.

Block 210 is that part of the process where the A/D converter is first read (identified in FIG. 11 as "A/D"). The A/D converter, as explained previously in connection with FIG. 6, comprises the circuitry which generates a digital signal representative of the energy content of the raw signal from the sensor 72. As such, the output of the A/D converter read at block 210 may be thought of as equivalent to the sensor level index signal previously described.

Note that at block 210, in addition to reading the A/D converter, the algorithm also checks the battery voltage to determine if the recommended replacement time (RRT) threshold has been reached. If so, a special branch is taken to block 212 where, rate responsive pacing is terminated and pacing continues at base rate and, when the reed switch is on, control is passed back to the "Resume" point at the top of the flow chart. This causes the Communication Algorithm to again be entered; which action, in turn, communicates through the telemetry channel the fact that RRT has been sensed.

If, when the battery voltage is measured, RRT has not occurred, then the A/D converter is started for a second sample, and control passes to block 214. Block 214 is the heart of the rate-responsive algorithm because it is at this point that various time intervals are recalculated based upon the sensor level index signal obtained from the A/D converter. In other words, it is at this point in the algorithm where the information obtained from the activity sensor is first used. It is also at this time that the event and histogram data are stored.

After all of the calculations defined in block 214 are completed, another check is made of the reed switch to determine whether it is on or off. If it is off, then control passes to Scan 1, block 206, which is similar to Scan 2, block 215, and the cycle begins over again. If the reed switch is on, then programming changes are being made, or information is desired, so control returns to communications, block 200.

It may thus be seen that the present invention provides a versatile and efficacious rate-responsive pacer wherein the pacing rate of the pacer is altered whenever the energy level of the sensor's raw signal, referred to as exercise level, is above a low limit. This low limit is referred to as the rate response threshold. The rate response threshold is either fixed, having settings of from 1 to 7, or automatic, having a setting of "auto". Automatic rate response threshold is preferably a long term average (approximately 18 hours) of sensor input plus a fixed offset of two.

The offset is added to the sensor input to avoid increases in rate due to very small increases in exercise level. When the exercise level falls below the rate response threshold, or low limit, the pacing rate is the basic rate. When exercise level is above the low limit, or rate response threshold, the static pacing rate will increase above the basic rate according to a specified slope curve which relates exercise level to pacing rate at a specified response time rate (see FIG. 3). (It should be noted that when the sensor is off, and the pacer is programmed to operate in the DDD mode, P-wave tracking will also increase the pacing rate. However, P-wave tracking increases the pacing rate independently of the curves shown in FIG. 3.)

Slope is selectable from 16 curves which provide low to high responsiveness, i.e., curve steepness. The selected curve is translated to the low limit and base rate intersection. The curve is truncated at an upper rate referred to as maximum sensor-indicated rate. Exercise levels above the value corresponding to maximum sensor-indicated rate do not produce a higher pacing rate. Rather, pacing continues at the maximum rate.

Pacing follows the slope curve after the sensed exercise level is processed by a rate acceleration/deceleration limiting algorithm. For rapid changes upward in exercise level, there is a minimum time between incremental increases in pacing rate. This limit is controlled by a parameter referred to as reaction time. Reaction time may be viewed as the total minimum time allowed for a rate increase from, for example, a base rate of 60 ppm, which is the programmed pacing rate at rest, to a maximum sensor rate of 150 ppm, which is the maximum pacing rate allowed due to exercise.

Similarly, for rapid changes downward in exercise level, there is a minimum time between incremental decrease in pacing rate. This limit is controlled by a parameter referred to as recovery time. Recovery time may be viewed as the total minimum time allowed for a rate decrease from, for example, a rate of maximum sensor 150 ppm to a base rate of 60 ppm.

The autothreshold feature may be initialized from an external programmer 38. An initial value of the automatic rate response threshold is determined by running the pacing algorithm for 30 pacing intervals in order to develop a 30 cycle sensor average. Thereafter, as more sensor data is made available, the sensor level index signal is averaged over a prescribed period of time (much longer than 30 cycles, preferably long enough to be predominated by low level activity, such as 18 hours) in order to provide a continuous indication of what the rate response threshold value should be. The rate response threshold value is set at this long-term running average with an appropriate offset added thereto.

Although an exemplary embodiment of the present invention has been shown and described, it will be apparent to those having ordinary skill in the art that a number of changes, modifications, or alterations to the invention as described herein may be made, none of which depart from the spirit of the present invention. For example, while the sensor described herein is a piezoelectric activity sensor, it is to be understood that other types of sensors could be used, including any of numerous physiological sensors which generate a sensor signal which varies as a function of the physiological environmental to which the sensor is subjected. All such changes, modifications, and alterations should therefore be seen as within the scope of the present invention.

What is claimed is:

1. A rate-responsive pacemaker comprising:
    pulse generator means for generating pacing pulses at a rate set by a rate control signal;
    means for generating a base rate signal;
    sensor means for generating a raw sensor signal having a value that varies as a function of a sensed physiological parameter;
    processor means for generating a pacing rate signal as a function of said raw sensor signal, wherein said processor means comprises:
       preprocessing means for generating one of a plurality of sensor level index signals as a function of the value of said raw sensor signal, said plurality of sensor level index signals including a minimum sensor level index signal corresponding to all values of said raw sensor signal below a first prescribed threshold, and a maximum sensor level index signal corresponding to all values of said raw sensor signal above a second prescribed threshold; and
       conversion means for converting said one of a plurality of sensor level index signals to said pacing rate signal;
    and
    selection means for selecting one of said base rate signal or said pacing rate signal as the rate control signal for said pulse generator means, whereby said pulse generator means generates said pacing pulses at a rate determined by the selected one of said base rate signal or said pacing rate signal.

2. The rate-responsive pacemaker of claim 1 wherein said conversion means comprises:
    memory means for storing pacing rate data which defines a prescribed relationship between each of said plurality of sensor level index signals and the pacing rate signal; and
    means for retrieving and processing the pacing rate data from said memory means in order to generate a particular pacing rate signal corresponding to said one of a plurality of sensor level index signals generated by said preprocessing means.

3. The rate-responsive pacemaker of claim 2, further comprising:
    means for generating programming signals; and
    telemetry means within said rate-responsive pacemaker for receiving said programming signals and transferring them to said base rate signal generating means and processor means, said base rate signal generating means and processor means both including means for responding to said programming signals so as to alter the operating of said base rate signal generating means and said processor means in a manner indicated by said programming signals, whereby the operation of said rate-responsive pacemaker can be selectively programmed with said programming signals.

4. The rate-responsive pacemaker of claim 3 wherein said programming signals include memory signals for altering the pacing rate data stored in the memory means of the conversion means of said processor means.

5. The rate-responsive pacemaker of claim wherein said conversion means comprises:
    a plurality of transfer functions, each transfer function of said plurality of transfer functions defining a particular relationship between all of said plurality of sensor level index signals and a pacing rate corresponding to each of said sensor level index signals;
    means for programmably selecting one of said plurality of transfer functions to define the relationship between said sensor level index signals and the pacing rate signal.

6. The rate-responsive pacemaker of claim 5 wherein each transfer function of said plurality of transfer functions defines a minimum sensor level index signal below which the pacing rate defined by the transfer function does not change, and a maximum sensor level index signal above which the pacing rate defined by the transfer function does not change.

7. The rate-responsive pacemaker of claim 6 wherein said conversion means further comprises:
    rate response threshold means for selectively altering the minimum sensor level index signal below which the pacing rate signal does not change; whereby when said selection means selects the pacing rate signal as the rate control signal for said pulse generator means, the rate at which said pulse generator means generates said pacing pulses will not change unless the sensor level index signal obtained from said preprocessing means exceeds said minimum sensor level signal.

8. The rate-responsive pacemaker of claim 7 wherein said rate response threshold means further comprises:

monitoring means for monitoring the sensor level index signal over a prescribed period of time and for generating a first reference signal weighted by all of the sensor level index signals monitored over said prescribed period of time; and autothreshold means for automatically setting the minimum sensor level index signal below which the pacing rate signal does not change as a function of said first reference signal.

9. The rate-responsive pacemaker of claim 8 wherein said first reference signal comprises an average of the sensor level index signal monitored over said prescribed period of time.

10. The rate-responsive pacemaker of claim 9 wherein said prescribed period of time over which said sensor level index signal is averaged comprises at least 18 1 hours.

11. The rate-responsive pacemaker of claim 8 wherein said autothreshold means sets the minimum sensor level below which the pacing rate does not change at a prescribed number of increments above said first reference signal.

12. The rate-responsive pacemaker of claim 1 further comprising rate limiting means for limiting the rate at which the pacing rate can change within a prescribed period of time.

13. The rate-responsive pacemaker of claim 12 wherein said rate limiting means comprises:

reaction time means for limiting the rate at which the pacing rate can increase within said prescribed period of time to a first rate limit; and recovery time means for limiting the rate at which the pacing rate can decrease within said prescribed period of time to a second rate limit.

14. The rate-responsive pacemaker of claim 13 further comprising:

means for generating a programming signal;

telemetry means within said rate-responsive pacemaker for receiving said programming signal and transferring it to said processor means; and said processor means including means for responding to said programming signal so as to alter said first and second rate limits in a manner indicated by said programming signal.

15. In a pacemaker comprising an implantable housing; a battery within said housing; a pacemaker chip within said housing and connected to said battery; a connector block attached to said housing and said pacemaker chip to which a pacemaker lead may be detachably connected, the improvement comprising:

a microprocessor chip within said housing and connected to said pacemaker chip and said battery;

memory means coupled to said microprocessor chip for storing program data which controls the operation of said microprocessor chip;

sensor means for sensing a physiological parameter and for generating a raw sensor signal as a function thereof; and sensor circuit means for generating one of a plurality of sensor level signals as a function of the energy content of said raw sensor signal, and for presenting said sensor level signal to said microprocessor chip;

processing means included in said microprocessor chip, said processing means responsive to the program data stored in said memory means for generating a pacing rate signal which varies in a prescribed manner as a function of the sensor level signal, said pacing rate signal being presented to said pacemaker chip;

means, included in said pacemaker chip, for responding to said pacing rate signal in order to alter the rate at which pacing pulses are generated by said pacemaker.

16. The pacemaker of claim 15 wherein the sensor circuit means comprises means for generating one of a discrete number of sensor level signals as a function of the energy content of said raw sensor signal.

17. The pacemaker of claim 15 wherein the number of discrete sensor level signals is at least thirty-two.

18. The pacemaker of claim 15 wherein said prescribed manner in which said pacing rate signal varies as a function of the sensor level signal comprises a lower pacing rate limit whenever said sensor level signal is less than a low rate response threshold value, and an upper pacing rate limit whenever said sensor level signal is greater than a maximum rate response level, and one of a plurality of intermediate pacing rate values whenever said sensor level signal is between said low rate response threshold value and said maximum rate response level, there being an intermediate pacing rate value for each sensor level signal falling between said low rate response threshold value and said maximum rate response level.

19. The pacemaker of claim 18 wherein the low rate response threshold value of said sensor level signal is programmably selectable.

20. The pacemaker of claim 18 wherein said processing means of said microprocessor chip comprises:

means for monitoring and processing the sensor level signal generated by said sensor circuit means over a prescribed period of time and for generating a reference sensor signal as a result of said monitoring and processing; and further wherein the low rate response threshold value of said sensor level signal is automatically setable by said processing means to a value derived from said reference sensor signal.

21. The pacemaker of claim 15 wherein said pacemaker chip further comprises:

means for selectively receiving said pacing rate signal from said microprocessor chip, said pacemaker chip including means for referencing a base rate pacing signal in the event said pacing rate signal is not received; whereby the pacemaker produces stimulation pulses at a rate determined by said base rate pacing signal when said pacing rate signal is not received from said microprocessor chip, and at a rate determined by said pacing rate signal when said pacing rate signal is received from said microprocessor chip.

22. The pacemaker of claim 21 wherein said microprocessor chip further comprises:

means for storing said pacing rate signal over a prescribed period of time regardless of whether said pacing rate signal is received by said pacemaker chip.

23. The pacemaker of claim 22 further comprising:

means for producing histogram reports indicative of the pacing rate signals stored by said microprocessor means during said prescribed time period.

24. A rate-responsive pacemaker comprising:

a pulse generator having means for generating pulses at a prescribed rate;

state logic means for controlling said pulse generator, including whether a pulse is to be generated and, if so, at what rate, said state logic means comprising:
state logic registers which, in combination, assume one of a possible plurality of states as a function of signals applied thereto;
memory circuitry addressed by said state logic registers, said memory circuitry having prescribed control signals stored therein at each location which is addressable by said state logic;
timing circuitry which generates timing signals;
sensing circuitry which generates event signals at the occurrence of prescribed events; and
logic circuitry responsive to said control signals, timing signals and event signals having output signals which steer said state logic registers as a function of said control, timing and event signals, said state logic registers continuously cycling through various states as a function of the control, timing and event signals applied to said logic circuitry, a pacing cycle comprising a cycle of said state logic from a prescribed reference state, to at least one other state, and back to said reference state;
a physiological sensor which generates a raw sensor signal having an energy content that varies as a function of a physiological environment to which said physiological sensor is subjected;
a conversion circuit coupled to said sensor, said conversion circuit including means for monitoring the energy content of said raw sensor signal and means for generating a discrete sensor level index signal as a function of said energy content at least once each pacing cycle, said sensor level index signal thereby assuming one of a plurality of possible sensor level signal values once each pacing cycle;
processor means coupled to said conversion circuit for defining a sensor indicated rate signal as a function of the sensor level index signal for each pacing cycle; and
interface means positioned between said processor means and the memory circuitry of said state logic means for selectively injecting said sensor indicated rate signal into the control signals of said memory circuitry that is presented to said logic circuitry, whereby said sensor indicated rate signal, when so injected, cooperates with the event and timing signals already present to influence the rate at which pulses are generated by said pulse generator.

25. The rate-responsive pacemaker of claim 24 wherein said means for measuring the energy content of said raw sensor signal comprises:
a rectifying and filter circuit which produces an analog signal having a level which varies as a function of the energy content of said raw sensor signal; and
an analog-to-digital conversion circuit which converts said analog signal to a digital signal at least once each pacing cycle, said digital signal comprising said sensor level index signal for that particular pacing cycle.

26. The rate-responsive pacemaker of claim 25 wherein said conversion circuit comprises:
means for converting said raw sensor signal to one of n possible discrete sensor level index signals, n being an integer greater than ten, a first of said sensor level index signals corresponding to said analog signal having a magnitude which is less than 1/nth of a maximum possible magnitude of said analog signal, a second of said sensor level index signals corresponding to an analog signal having a magnitude which is less than 2/nths of the maximum possible magnitude of said analog signal but greater than 1/nth of the maximum magnitude of said analog signal, a third of said sensor level index signals corresponding to an analog signal having a magnitude which is less than 3/nths of the maximum possible magnitude of said analog signal but greater than 2/nths of the maximum possible magnitude of said analog signal, and so on, up to an nth of said sensor level index signals corresponding to an analog signal having a magnitude which is greater than $(n-1)$/nths of the maximum possible magnitude of said analog signal.

27. The rate-responsive pacemaker of claim 24 wherein said conversion circuit comprises:
means for converting said raw sensor signal to one of n possible discrete sensor level index signals, being an integer greater than ten, a first of said sensor level index signals corresponding to a raw sensor signal having an energy content which falls within a first defined energy zone of said raw sensor signal, a second of said sensor level index signals corresponding to a raw sensor signal having an energy content which falls within a second defined energy zone of said raw sensor signal, a third of said sensor level index signals corresponding to a raw sensor signal having an energy content which falls within a third defined energy zone of said raw sensor signal, and so on, up to an nth of said sensor level index signals corresponding to a raw sensor signal having an energy content which falls within an nth defined energy zone of said raw sensor signal.

28. The rate-responsive pacemaker of claim 27 wherein said n defined energy zones of said raw sensor signal are zones of equal energy.

29. The rate responsive pacemaker of claim 27 wherein the sensor indicated rate signal defined by said processor means is a predefined minimum value when said sensor level index signal is less than a prescribed rate response threshold, and wherein the sensor indicated rate signal assumes one of a possible plurality of predefined values greater than said minimum value as a function of said sensor level index signal when said sensor level index signal is greater than or equal to said prescribed rate response threshold.

30. The rate-responsive pacemaker of claim 29 further including programming means for programmably setting the prescribed rate response threshold.

31. The rate-responsive pacemaker of claim 29 wherein said processor means comprises:
means for monitoring and processing the sensor level index signal for a prescribed number of prior cardiac cycles and means for automatically generating said prescribed rate response threshold as a function of said monitoring and processing.

32. The rate-responsive pacemaker of claim 29 wherein said processor means comprises:
means for monitoring and processing the sensor level index signal for a prescribed period of time and means for automatically generating said prescribed rate response threshold as a function of said monitoring and processing.

33. The rate-responsive pacemaker of claim 32 wherein said means for monitoring and processing comprises:

means for averaging the sensor level index signal during said prescribed period of time, and wherein said means for automatically generating said prescribed rate response threshold comprises means for defining said prescribed rate response threshold to be the average sensor level index signal computed over the prescribed period of time plus an offset index signal.

34. The rate-responsive pacemaker of claim 33 wherein the number n of said sensor level index signals comprises thirty-two, each of said sensor level index signals having a value representative of the integers 0 through 31, and further wherein said offset index signal comprises two, whereby if the average sensor level index signal for the prescribed period of time is computed to be, for example, five, the prescribed rate response threshold is automatically set at a value two more than five, or seven.

35. The rate-responsive pacemaker of claim 34 wherein the prescribed period of time over which the sensor level index signal is averaged comprises eighteen hours.

36. A rate-responsive pacing system comprising:
implantable pulse generator means for generating a pacing pulse at a rate set by a rate control signal;
means for generating a base rate signal;
implantable sensor means for generating a raw sensor signal indicative of a need to change the rate at which said pacing pulses generated by said pulse generator means;
implantable processor means coupled to said pulse generator means and said sensor means for generating a sensor indicated rate signal;
selection means for programmably selecting one of said base rate signal or said sensor indicated rate signal as the rate control signal controlling said pulse generator means; and
automatic reversion means coupled to said selecting means for automatically causing said selection means to select one of said base rate signal or said sensor indicated rate signal as the rate control signal in the event the other of said base rate signal or said sensor indicated rate signal is not generated.

37. The rate-responsive pacing system of claim 36 wherein said processor means comprises:
means for converting said raw sensor signal into one of a plurality of sensor level index signals at prescribed sample times, said conversion causing one of said plurality of sensor level index signals to be generated as a function of the magnitude of said raw sensor signal at the sample time, and further wherein said processor means includes means for defining said sensor indicated rate signal to assume a value which varies as a function of the sensor level index signal for that sample time.

38. The rate-responsive pacing system of claim 37 wherein the sensor indicated rate signal defined by said processor means is a predefined minimum value when said sensor level index signal is less than a prescribed rate response threshold, and wherein the sensor indicated rate signal assumes one of a possible plurality of predefined values greater than said minimum value as a function of said sensor level index signal when said sensor level index signal is greater than or equal to said prescribed rate response threshold.

39. The rate-responsive pacemaker of claim 38 further including programming means for programmably setting the prescribed rate response threshold.

40. The rate-responsive pacemaker of claim 38 wherein said processor means comprises:
means for monitoring and processing the sensor level index signal for a prescribed period of time, and means for automatically generating said prescribed rate response threshold as a function of said monitoring and processing.

41. The rate-responsive pacemaker of claim 40 wherein said means for monitoring and processing comprises:
means for averaging the sensor level index signal during said prescribed period of time, and wherein said means for automatically generating said prescribed rate response threshold comprises means for defining said prescribed rate response threshold to be the average sensor level index signal computed over the prescribed period of time plus an offset index signal.

42. The rate-responsive pacemaker of claim 37 wherein said processor means further comprises:
histogram means for selectively storing said sensor indicated rate signals over a selectable period of time, and for providing said stored signals as histogram data upon request.

43. In a rate-responsive pacemaker having means for generating a pacing pulse on demand at a rate determined by a sensor indicated rate signal, said sensor indicated rate signal assuming a value as a function of one of a possible plurality of sensor index signals, said sensor index signals being derived from a sensor adapted to sense a parameter that indicates the rate at which pacing pulses generated by the pacemaker should change, said pacemaker further having histogram memory means for storing said sensor indicated rate signals over time, a method of setting a selectable rate response threshold value for said sensor index signals below which said sensor indicated rate signal remains constant at a minimum sensor indicated rate value and above which said sensor indicated rate signal varies as a function of said sensor index signal, said method comprising the steps of: (a) subjecting said pacemaker to a low level of activity; (b) sampling said sensor indicated rate signal at a prescribed sampling rate during said low level activity period; (c) sorting and storing each sampled sensor indicated rate signal in said hidtogram memory means as a function of its value; (d) retrieving and displaying the stored values of said sampled sensor indicated rate signals; and (e) selecting said rate response threshold value for said sensor index signals to be at least a value which corresponds to the highest sensor indicated rate signal displayed during said low activity period.

44. The method of claim 43 wherein step (e) comprises selecting said rate response threshold value for said sensor index signals to be a prescribed number of increments above the sensor level index signal which corresponds to the highest sensor indicated rate signal displayed during said low activity period.

45. In a rate-responsive pacemaker having means for generating a pacing pulse on demand at a rate determined by a sensor indicated rate signal, said sensor indicated rate signal assuming a value as a function of one of a possible plurality of sensor index signals, said sensor index signals being derived from a sensor adapted to sense a parameter that indicates the rate at which pacing pulses generated by the pacemaker should change, said pacemaker further having processing means for processing said sensor index signals over time, a method of automatically setting a rate response threshold value for said sensor index signals below which said sensor indicated rate signal remains constant and above which said sensor indicated rate signal varies as a function of said sensor index signal, said method comprising the steps of: (a) subjecting said pacemaker to a known level of activity for a prescribed period of time; (b) processing said sensor index signals to determine a representative sensor index signal over said prescribed period of time; (c) adding a selectable offset value to the representative sensor index signal determined in step (b), and (d) using the value computed in step (c) as said rate response threshold value.

46. The method of claim 45 wherein step (b) comprises processing said sensor index signal over said prescribed period of time to determine the average sensor index signal over said period of time.

47. The method of claim 45 wherein steps (b) through (d) are carried out automatically by said processing means.

* * * * *

UNITED STATES PATENT AND TRADEMARK OFFICE
CERTIFICATE OF CORRECTION

PATENT NO. : 4,940,052

DATED : July 10, 1990

INVENTOR(S) : Mann, Brian M. and Poore, John W.

It is certified that error appears in the above—identified patent and that said Letters Patent is hereby corrected as shown below:

Claim 36, col. 27, line 38:

Change "selecting" to read --selection--.

Signed and Sealed this

Twenty-eighth Day of April, 1992

Attest:

HARRY F. MANBECK, JR.

*Attesting Officer*      *Commissioner of Patents and Trademarks*